US009624301B2

(12) United States Patent
Kumar et al.

(10) Patent No.: US 9,624,301 B2
(45) Date of Patent: Apr. 18, 2017

(54) POLYNUCLEOTIDES ENCODING AN ACTRIIB ANTIBODY

(71) Applicants: Acceleron Pharma Inc., Cambridge, MA (US); Dyax Corp., Burlington, MA (US)

(72) Inventors: Ravindra Kumar, Acton, MA (US); Asya Grinberg, Lexington, MA (US); Monique Davies, Harpswell, ME (US); Diana Martik, Cambridge, MA (US); Janja Cosic, Arlington, MA (US); Rachel Kent, Boxborough, MA (US); David Buckler, Chester, NJ (US)

(73) Assignees: Acceleron Pharma Inc., Cambridge, MA (US); Dyax Corp., Burlington, MA (US)

( * ) Notice: Subject to any disclaimer, the term of this patent is extended or adjusted under 35 U.S.C. 154(b) by 0 days.

(21) Appl. No.: 15/234,581

(22) Filed: Aug. 11, 2016

(65) Prior Publication Data

US 2016/0347845 A1 Dec. 1, 2016

Related U.S. Application Data

(63) Continuation of application No. 14/508,988, filed on Oct. 7, 2014, now abandoned, which is a continuation of application No. 13/828,419, filed on Mar. 14, 2013, now abandoned, which is a continuation of application No. 13/283,552, filed on Oct. 27, 2011, now Pat. No. 8,765,385.

(51) Int. Cl.
*C07K 16/28* (2006.01)

(52) U.S. Cl.
CPC ...... *C07K 16/2863* (2013.01); *C07K 2317/55* (2013.01); *C07K 2317/56* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,914,128 | B1 | 7/2005 | Salfeld et al. |
| 7,052,873 | B2 | 5/2006 | Tsuchiya |
| 7,842,663 | B2 | 11/2010 | Knopf et al. |
| 7,947,646 | B2 | 5/2011 | Sun et al. |
| 8,110,355 | B2 | 2/2012 | Atwood et al. |
| 8,388,968 | B2 | 3/2013 | Berger et al. |
| 2010/0272734 | A1 | 10/2010 | Berger et al. |
| 2012/0237521 | A1 | 9/2012 | Berger et al. |
| 2013/0108650 | A1 | 5/2013 | Kumar et al. |
| 2013/0344091 | A1 | 12/2013 | Berger et al. |
| 2014/0199317 | A1 | 7/2014 | Seehra et al. |

FOREIGN PATENT DOCUMENTS

| | | | |
|---|---|---|---|
| WO | WO 2010/125003 | A1 | 11/2010 |
| WO | WO 2013/006437 | A1 | 1/2013 |

OTHER PUBLICATIONS

Abbiotec: ACTR-IIA Antibody: Catalog No. 251303, <http://www.abbiotec.com/antibodies/actr-iia-antibody> ; retrieved from the internet Jun. 3, 2010.

ACTR-II (149/1): sc-57022, Santa Cruz Biotechnology, Inc.: http://datasheets.scbt.com/sc-57022.pdf, Dated Jun. 3, 2010.

ACTR-II (D-15): sc-5669, Santa Cruz Biotechnology, Inc.: http://datasheets.scbt.com/sc-5669.pdf, dated Jun. 3, 2010.

ACTR-II (H-65): sc-25451, Santa Cruz Biotechnology, Inc.: http://datasheets.sebt.com/se-25451.pdf, dated Jun. 3, 2010.

ACTR-IIA (A-24): sc-130679, Santa Cruz Biotechnology, Inc.: http://datasheets.scbt.com/sc-130679.pdf, dated Jun. 3, 2010.

ACTR-IIA (N-17): sc-5667, Santa Cruz Biotechnology, Inc.: http://datasheets.scbt.com/sc-5667.pdf, dated Jun. 3, 2010.

Beiboer et al., "Guided Selection of a Pan Carcinoma Specific Antibody Reveals Similar Binding Characteristics yet Structural Divergence between the Original Murine Antibody and its Human Equivalent," J. Mol. Biol., vol. 296: 833-849 (2000).

International Search Report (PCT/US2012/062321) dated Feb. 21, 2013.

Klimka, et al., "Human anti-CD30 recombinant antibodies by guided phage antibody selection using cell panning," British Journal of Cancer. vol. 83: 252-260 (2000).

Mariuzza, R.A., "The Structural Basis of Antigen-Antibody Recognition," Ann. Rev. Biophys. vol. 16: 139-159 (1987).

Pennucci et al., Multiplexed evaluation of a cell-based assay for the detection of antidrug neutralilzing antibodies to Panitumumab in human serum using automated fluorescent microsopy,: J. Biomol. Sceen. vol. 15: 644-652 (2010).

R&D Systems Catalogue No. AF339 Datasheet: Human Activin RIIB Antibody [retrieved on Feb. 13, 2013] Retrieved from the Internet: http://www.mdsystems.com/pdf/af339.pdf.

R&D Systems, "Antibody Reference Guide and Catalog Instructions," [retrieved on Feb. 13, 2013]; http://web.archive.org/web/20090220022132/http://mdsystems.com/DAM_public/5658.pdf; published Mar. 14, 2009 as per the Wayback Engine. See, in particular: p. 3.

Rudikoff et al., "Single amino acid substitution altering antigen-binding specificity," Proc. Natl. Acad., Sci. USA, vol. 79: 1979-1983 (1982).

Sirskyj et al., Detection of influenza A and B neutralizing antibodies in vaccinated ferrets and macaques using specific biotinstreptavidin conjugated antibodies, J. Virol. Methods. vol. 163: 459-464 (2010).

Swanson et al., "Use of Biosensors to Monitor the Immune Response," Biologics, vol. 109: 71-78 (2000).

Swanson, S. J., "New Technologies for the Detection of Antibodies to Therapeutic Proteins," Immunogenicity of Therapeutics Biological Products, vol. 112: 127-133 (2003).

(Continued)

*Primary Examiner* — Elly-Gerald Stoica
(74) *Attorney, Agent, or Firm* — Ropes & Gray LLP

(57) ABSTRACT

The disclosure provides, among other aspects, neutralizing antibodies and portions thereof that bind to ActRIIB and uses for same.

4 Claims, 3 Drawing Sheets
(3 of 3 Drawing Sheet(s) Filed in Color)

(56) References Cited

OTHER PUBLICATIONS

Thorpe and Swanson, "Current methods for Detecting Antibodies against Erythropoietin and Other Recombinant Proteins," Clinical and Diagnostic Laboratory Immunology, vol. 12(1): 28-39 (2005).
US Biological Technical Data Sheet for A0856-1A, accessed on Feb. 20, 2013.
US Biological, Activin Receptor Type IIA (RIIA) A0856-05E www.usbio.net/technicalsheet.php?item=A0856-05E dated Jun. 8, 2010.
Wong et al., "Validation parameters for a novel biosensor assay which simultaneously measures serum concentrations of a humanized monoclonal antibody and detects induced antibodies," Journal of Immunological Methods, vol. 209: 1-15 (1997).

A 25°C

B 37°C

POLYNUCLEOTIDES ENCODING AN ACTRIIB ANTIBODY

RELATED APPLICATION

This application is a continuation of U.S. application Ser. No. 14/508,988, filed Oct. 7, 2014, which is a continuation of U.S. application Ser. No. 13/828,419, filed Mar. 14, 2013 (now abandoned), which is a continuation of U.S. application Ser. No. 13/283,552, filed Oct. 27, 2011(now U.S. Pat. No. 8,765,385). The specifications of each of the foregoing applications are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Aug. 9, 2016, is named PHPH064104_Seq.txt and is 26,589 bytes in size.

BACKGROUND OF THE INVENTION

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The superfamily includes proteins that are variously described as Growth and Differentiation Factors (GDFs), Bone Morphogenetic Proteins (BMPs), activins and inhibins.

By manipulating the activity of a member of the TGF-beta superfamily, it is often possible to cause significant physiological changes in an organism. For example, GDF8 (myostatin) is a well-known regulator of skeletal muscle mass and strength. The Piedmontese and Belgian Blue cattle breeds carry a loss-of-function mutation in the myostatin gene that causes a marked increase in muscle mass. Grobet et al., Nat Genet. 1997, 17(1):71-4. Furthermore, in humans, inactive alleles of GDF8 are associated with increased muscle mass and, reportedly, exceptional strength. Schuelke et al., N Engl J Med 2004, 350:2682-8. Other members of the superfamily, such as activin A, are also reported to regulate skeletal muscle. Modulators of GDF8 and activin are in clinical development for the treatment of muscle conditions. Antibodies directed to myostatin promote muscle formation in animal models, although results in human clinical trials have not demonstrated prominent increases in skeletal muscle mass or strength, raising a question as to whether other members of the TGF-beta superfamily may regulate muscle growth. Walker et al., Ann Neurol. 2008, 63:561-71. The activin receptor type IIB (ActRIIB, also known as ACVR2B), is a high affinity receptor for myostatin, activin A and other members of the TGF-beta superfamily, including GDF11 and other activins. Lee et al. Proc Natl Acad Sci USA 2005, 102:18117-22; Mathews et al. Science 1992 255:1702-5; WO 00/43781; WO 2006/012627. An ActRIIB-Fc fusion protein acts as a high affinity antagonist to each of these ligands and promotes substantial muscle growth in animal models as well as humans. Lee et al. Proc Natl Acad Sci USA 2005, 102:18117-22; WO 2004/039948; WO 2006/012627; WO 2008/097541. ActRIIB-Fc is also known to promote bone formation and, in some cases, affect other tissues. WO 95/10611; Hamrick et al. Calcif Tissue Int 2002, 71:63-68; WO 2006/012627; WO 2008/097541. Similarly, it has been proposed that antibodies that bind to ActRIIB and disrupt ligand binding and/or signaling (e.g., neutralizing antibodies) can be used to promote muscle or bone formation and treat a variety of disorders. U.S. Pat. No. 6,656,475; WO 2006/012627; WO 2008/097541.

Thus, it is an object of this disclosure to provide antibodies that bind to ActRIIB and uses for same.

SUMMARY OF THE INVENTION

The disclosure provides, among other aspects, antibodies and fragments thereof that bind to ActRIIB and inhibit ActRIIB-mediated signaling. A variety of uses for such proteins are described herein. For example, the antibodies may be used to treat a variety of diseases, including disorders of skeletal muscle and bone, and as part of assays to identify known and novel ActRIIB-binding agents. In a further embodiment, antibodies that bind to ActRIIB and inhibit ligand binding may be used in assays to detect and characterize antibodies that may be generated in a human in response to administration of a polypeptide comprising a part or all of the extracellular domain of ActRIIB, such as an ActRIIB-Fc fusion protein.

In certain embodiments, the disclosure relates to antibodies, and fragments of antibodies (e.g., Fab, scFv) that specifically bind to ActRIIB. The binding agents can be characterized by their ability to inhibit binding to or signaling through ActRIIB by one or more ligands, such as myostatin, GDF11, activin A, activin B or others described in the art. Binding agents may cross-block the binding of at least one antibody disclosed herein, such as Ab-17G05, to ActRIIB and/or to be cross-blocked from binding ActRIIB by at least one of said antibodies. In certain aspects, the anti-ActRIIB antibody is a therapeutic antibody or functional fragment thereof. An anti-ActRIIB antibody or functional fragment thereof may bind to a ligand-binding domain of ActRIIB, the boundaries and attributes of which are described herein. An anti-ActRIIB antibody or functional fragment thereof may bind to ActRIIB between amino acids 19-134 of SEQ ID NO: 1. Any of the antibodies and fragments described herein may bind to ActRIIB with a KD (dissociation constant) of 1 nM, 100 pM, 50 pM, 20 pM, 10 pM or less. An anti-ActRIIB antibody may inhibit the binding of one or more ligands to ActRIIB, including myostatin, activin A, GDF11, activin B, BMP9 or BMP10. Because both activins and myostatin, and possibly GDF11, act as negative regulators of skeletal muscle mass, an anti-ActRIIB antibody may be selected so as to inhibit the binding of two of more of the aforementioned ligands to ActRIIB. An anti-ActRIIB antibody may inhibit the signaling caused by an ActRIIB ligand, such as myostatin, and such signaling may be measured by a Smad dependent reporter gene assay, such as the A204 assay described in the Examples. Smad activation may also be assessed by measuring the levels of phosphor-Smads, particularly Smad2 or Smad3. In certain instances, it will be desirable to selectively bind ActRIIB with little or no binding to the related receptor ActRIIA, and accordingly, an anti-ActRIIB antibody or functional fragment thereof may bind to ActRIIB with a 10-fold, 20-fold, 50-fold, 100-fold, 200-fold, 500-fold or 1000-fold or greater/better affinity than it binds to ActRIIA. An anti-ActRIIB antibody or functional fragment thereof may be of any of the known immunoglobulin isotypes, and particularly IgG1, IgG2 or IgG4, and may have an altered effector function. An altered effector function may be achieved by modifying or mutating the Fc region, and this may be performed to create an antibody having reduced ADCC or CDC reactivity. An anti-ActRIIB antibody or fragment thereof may promote skeletal muscle growth in vivo, particularly in a mouse, non-human primate or a human.

An anti-ActRIIB antibody or fragment thereof may comprise at least one CDR sequence having at least 80%, 85%, 90%, 91%, 92%, 93%, 94%, 95%, 96%, 97%, 98%, 99% or 100% identity to a CDR selected from the group consisting of SEQ ID NOs: 37-42. The antibody or fragment thereof may comprise at least two, three, four, five or six of the foregoing CDR sequences and may, for example, comprise three CDRs, CDR-H1, CDR-H2, and CDR-H3 wherein CDR-H1 comprises a sequence that is at least 80%, 85%, 90%, 91%, 92%, 93%, 94%, 95%, 96%, 97%, 98%, 99% or 100% identical to SEQ ID NO: 37, CDR-H2 comprises a sequence that is at least 80%, 85%, 90%, 91%, 92%, 93%, 94%, 95%, 96%, 97%, 98%, 99% or 100% identical to SEQ ID NO: 38, and CDR-H3 comprises a sequence that is at least 80%, 85%, 90%, 91%, 92%, 93%, 94%, 95%, 96%, 97%, 98%, 99% or 100% identical to SEQ ID NO: 39. The antibody or fragment thereof may comprise three CDRs, CDR-L1, CDR-L2, and CDR-L3, wherein CDR-L1 comprises a sequence that is at least 80%, 85%, 90%, 91%, 92%, 93%, 94%, 95%, 96%, 97%, 98%, 99% or 100% identical to SEQ ID NO: 40, CDR-H2 comprises a sequence that is at least 80%, 85%, 90%, 91%, 92%, 93%, 94%, 95%, 96%, 97%, 98%, 99% or 100% identical to SEQ ID NO: 41, and CDR-H3 comprises a sequence that is at least 80%, 85%, 90%, 91%, 92%, 93%, 94%, 95%, 96%, 97%, 98%, 99% or 100% identical to SEQ ID NO: 42. Other combinations and permutations of the foregoing CDR sequences and variants are included within the disclosure. An anti-ActRIIB antibody may comprise a heavy chain wherein said heavy chain comprises a polypeptide having at least 80%, 85%, 90%, 91%, 92%, 93%, 94%, 95%, 96%, 97%, 98%, 99% or 100% identity to the sequence given in SEQ ID NO: 15. An anti-ActRIIB antibody may comprise a light chain wherein said light chain comprises a polypeptide having at least 80%, 85%, 90%, 91%, 92%, 93%, 94%, 95%, 96%, 97%, 98%, 99% or 100% identity to the sequence given in SEQ ID NO: 16. An anti-ActRIIB antibody may comprise any combination of the foregoing heavy chain and light chain sequences.

The anti-ActRIIB antibodies and functional fragments described may be formulated as pharmaceutical compositions comprising such antibody or functional fragment. A pharmaceutical composition may comprise a pharmaceutically acceptable diluent or carrier.

In certain aspects the disclosure provides isolated polynucleotide sequences encoding the antibody or functional fragment thereof described herein, including any of the polynucleotides encoding each of the heavy and light chains described, as well as the variable domains and the respective CDR portions. The disclosure further provides cloning or expression vectors comprising any of the foregoing isolated polynucleotide sequences, and cells, particularly host cells such as CHO or NSO cells comprising any of the above nucleic acids or vectors. Such host cells may be used to produce the anti-ActRIIB antibodies described. In certain aspects the disclosure provides processes for the production of an antibody or functional fragment thereof described herein, comprising culturing a host cell comprising a cloning or expression vector encoding the antibody or functional fragment thereof, and isolating the antibody or functional fragment thereof.

A variety of uses for binding agents that neutralize ActRIIB have been described, and thus in certain aspects, the disclosure provides methods for using anti-ActRIIB antibodies or functional fragments. For example, such agents, and pharmaceutical preparations containing same, may be used in a method of treating a patient suffering from a musculoskeletal disease or disorder; acute and/or chronic renal disease or failure; cancer; breast cancer; Parkinson's Disease; conditions associated with neuronal death; ALS; brain atrophy; dementia; anemia; liver, kidney and pulmonary fibrosis; one or more age-related condition; rhabdomyosarcoma; bone-loss inducing cancer. Such methods may comprise the step of: administering an effective dose of an antibody disclosed herein or functional fragment thereof to said patient. Examples of musculoskeletal diseases or disorders include muscle atrophy, myopathy, myotonia, a congential myopathy, nemalene myopathy, multi/minicore myopathy and myotubular (centronuclear) myopathy, mitochondrial myopathy, familial periodic paralysis, inflammatory myopathy, metabolic myopathy, a glycogen or lipid storage disease, dermatomyositisis, polymyositis, inclusion body myositis, myositis ossificans, rhabdomyolysis and myoglobinurias; a dystrophy, including Duchenne, Becker, myotonic, fascioscapulohumeral, Emery-Dreifuss, oculopharyngeal, scapulohumeral, limb girdle, Fukuyama, a congenital muscular dystrophy, or hereditary distal myopathy; osteoporosis; a bone fracture; short stature; dwarfism; prolonged bed rest; voluntary inactivity; and/or involuntary inactivity. As further examples, a patient being treated may be elderly, may have spent time in a zero gravity environment or may have undergone a period of inactivity, and treatment may be initiated prior to the aforementioned event. Such a patient may have a fracture to a limb or joint or have undergone or be about to undergo hip or knee replacement surgery.

In certain aspects, the disclosure provides methods for using anti-ActRIIB antibodies to detect ActRIIB in cells and tissues, and also in assays designed to detect or assess other antibodies that bind to ActRIIB. Reagents that include the ligand-binding portion of ActRIIB (e.g., an ActRIIB-Fc fusion protein) are in development as therapeutic agents, and as with all biologic products, it is of interest to determine whether such agents cause the production in patients of antibodies against the therapeutic protein and whether such antibodies are neutralizing. Accordingly, a method described herein for detecting or characterizing anti-ActRIIB antibodies in blood may comprise a step of contacting an ActRIIB polypeptide (e.g. a polypeptide comprising an ActRIIB ligand binding domain) with a neutralizing anti-ActRIIB antibody. In an embodiment, such a method may comprise (i) forming a mixture comprising a sample (e.g., a blood or serum sample from a patient treated with an ActRIIB-Fc fusion protein or a placebo), an ActRIIB polypeptide and a control antibody that is a known neutralizing anti-ActRIIB antibody; and (ii) measuring the amount of control antibody that is bound to the ActRIIB polypeptide, wherein the ActRIIB polypeptide is a polypeptide comprising a ligand binding domain of ActRIIB. A decrease in the amount of control antibody bound to the ActRIIB polypeptide relative to a standard indicates that the sample contains a neutralizing anti-ActRIIB antibody. The standard may be a mixture comprising the ActRIIB polypeptide and the control antibody. The standard may further comprise a sample that is known to contain no substantial amount of neutralizing anti-ActRIIB antibody, and may further comprise a sample that contains a known amount of neutralizing anti-ActRIIB antibody. In another format, the assay may comprise (i) forming a mixture comprising the sample, an ActRIIB polypeptide and a ligand that binds to ActRIIB; (ii) measuring the amount of ligand that is bound to the ActRIIB polypeptide and comparing the amount of ligand that is bound with a standard, wherein the standard is measured amount of ligand bound to the ActRIIB polypeptide in a mixture comprising the ActRIIB polypeptide, the ligand and a control antibody that is a known neutralizing anti-ActRIIB antibody, and wherein the ActRIIB polypeptide is a polypeptide comprising a ligand binding domain of ActRIIB. A comparison of the amount of ligand bound to the ActRIIB polypeptide in the mixture versus the amount of ligand bound to the ActRIIB polypeptide in the standard may be used to assess the presence or absence of a neutralizing anti-ActRIIB antibody in the sample, with decreased ligand binding indicating higher levels of neutralizing anti-ActRIIB antibody. The ligand may be any known ligand for ActRIIB and may be selected from the group consisting of: activin A, activin B, myostatin and GDF11. In each assay format, the sample may contain blood or a blood product, optionally from a patient treated with an ActRIIB-Fc fusion protein or a patient that has not been treated with an ActRIIB-Fc fusion protein. The neutralizing anti-ActRIIB antibody may be any of the anti-ActRIIB antibodies disclosed herein and may, for example comprise at least one CDR sequence having at least 80% identity to a CDR selected from the group consisting of SEQ ID NOs: 37-42 or may be the Ab-17G05.

These and other aspects of the present invention will become apparent upon reference to the following detailed description and attached drawings. All references disclosed herein are hereby incorporated by reference in their entireties as if each was incorporated individually.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

1. Overview

Figure 1:
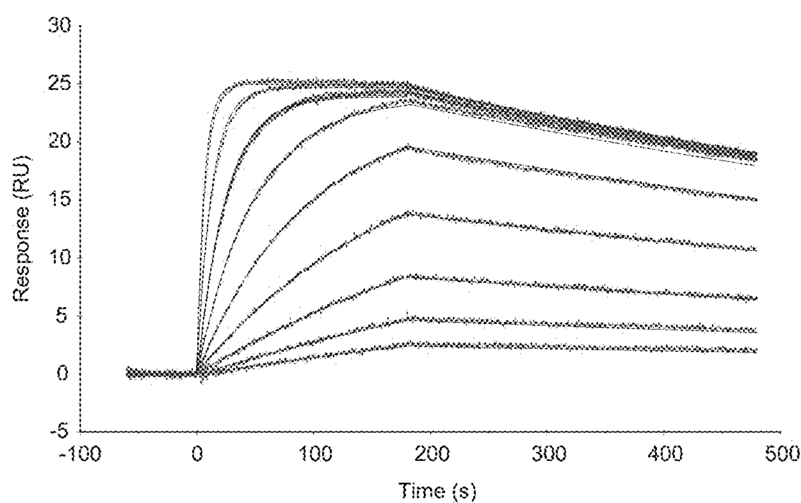
FIG. 1 depicts kinetic characterization of Fab-17G05 binding to hActRIIB-hFc as determined by BIACORE™-based analysis at 25° C. (A) or 37° C. (B). hActRIIB-hFc was captured on a chip with covalently immobilized antibody against human IgG1 Fc and then exposed to Fab-17G05 at concentrations ranging from 0.0195 μg/ml to 5 μg/ml. RU, response units. As determined by nonlinear regression, the $K_D$ was $5.5\times10^{-10}$ at 25° C. and $1.9\times10^{-9}$ at 37° C.
Figure 1:
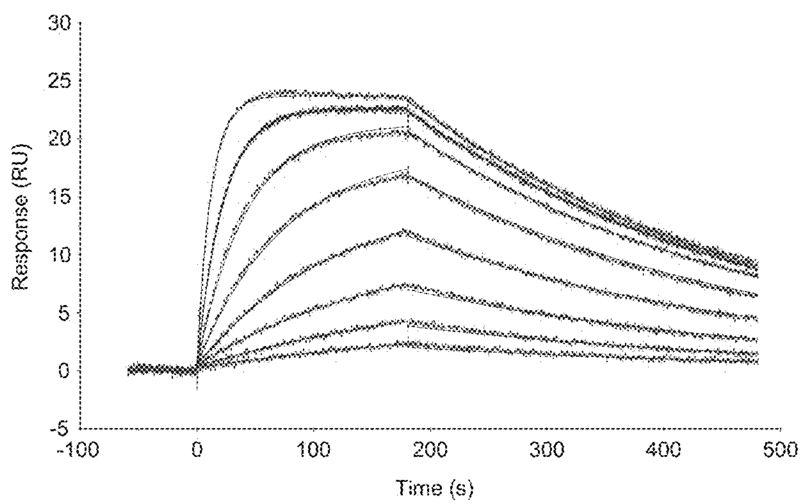

Activins are dimeric polypeptide growth factors that belong to the TGF-beta superfamily. There are three principal activin forms (A, B, and AB) that are homo/heterodimers of two closely related β subunits ($\beta_A\beta_A$, $\beta_B\beta_B$, and $\beta_A\beta_B$). The human genome also encodes an activin C and an activin E, which are primarily expressed in the liver. In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos (DePaolo et al., 1991, Proc Soc Ep Biol Med. 198:500-512; Dyson et al., 1997, Curr Biol. 7:81-84; Woodruff, 1998, Biochem Pharmacol. 55:953-963). In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Other proteins that may regulate activin bioactivity and/or bind to activin include follistatin (FS), follistatin-related protein (FSRP), $\alpha_2$-macroglobulin, Cerberus, and endoglin. Together with myostatin, activin has been implicated as a negative regulator of skeletal muscle mass. He et al. 2005 Anat Embryol (Berl) 209:401-407; Link and Nishi, Exp. Cell Res. 1997 233:350-62.

TGF-β superfamily signals are mediated by heteromeric complexes of type I and type II serine/threonine kinase receptors, which phosphorylate and activate downstream Smad proteins upon ligand stimulation (Massague, 2000, Nat. Rev. Mol. Cell Biol. 1:169-178). These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling; and type II receptors are required for binding ligands and for expression of type I receptors. Type I and II activin receptors form a stable complex after ligand binding, resulting in phosphorylation of type I receptors by type II receptors.

Two related type II receptors, ActRIIA and ActRIIB, have been identified as the type II receptors for activins (Mathews and Vale, 1991, Cell 65:973-982; Attisano et al., 1992, Cell 68: 97-108). Besides activins, ActRIIA and ActRIIB can interact biochemically with several other TGF-β family proteins, including BMP7, Nodal, BMP9, BMP10, GDF8, and GDF11 (Yamashita et al., 1995, J. Cell Biol. 130:217-226; Lee and McPherron, 2001, Proc. Natl. Acad. Sci. 98:9306-9311; Yeo and Whitman, 2001, Mol. Cell 7: 949-957; Oh et al., 2002, Genes Dev. 16:2749-54). ALK4 is the primary type I receptor for activins, particularly for activin A, and ALK-7 may serve as a receptor for activins as well, particularly for activin B.

Inhibitors of the activin signaling pathway have been proposed for treatment of a variety of disorders, including bone loss, various tumors including multiple myeloma and breast cancer, and anemia. Inhibitors of myostatin and GDF11 signaling have likewise been proposed for the treatment of a variety of disorders, including muscle disorders, neurological disorders and bone disorders. Neutralizing anti-ActRIIB antibodies that interfere with signaling by any or all of activin A, activin B, GDF8 or GDF11 may be used in a variety of indications for the treatment of muscle loss or insufficient muscle growth, including myopathies, muscular dystrophies, muscular atrophy, cachexia, and age-related conditions such as sarcopenia as well as for the treatment of bone disorders and various cancers.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "A") in the polymer sequence not containing the inserted or deleted residue. Unless indicated otherwise, BLAST shall be the default algorithm for comparisons.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

As used herein, the term "ActRIIB" refers to a family of activin receptor type IIB (ActRIIB) proteins from any species. Reference to ActRIIB herein is understood to be a reference to any one of the currently identified forms. Members of the ActRIIB family are generally transmembrane proteins, composed of a ligand-binding extracellular domain with a cysteine-rich region, a transmembrane domain, and a cytoplasmic domain with predicted serine/threonine kinase activity.

The human ActRIIB precursor protein sequence is as follows (NCBI Reference Sequence NM_001106.3), with the underlined sequence corresponding to the literature-reported mature extracellular domain, within which are epitopes targeted by neutralizing anti-ActRIIB antibodies and other ActRIIB binding agents.

```
                                          (SEQ ID NO: 1)
MTAPWVALALLWGSLCAGSGRGEAETRECIYYNANWELERTNQSGLERCE

GEQDKRLHCYASWRNSSGTIELVKKGCWLDDFNCYDRQECVATEENPQVY

FCCCEGNFCNERFTHLPEAGGPEVTYEPPPTAPTLLTVLAYSLLPIGGLS

LIVLLAFWMYRHRKPPYGHVDIHEDPGPPPPSPLVGLKPLQLLEIKARGR

FGCVWKAQLMNDFVAVKIFPLQDKQSWQSEREIFSTPGMKHENLLQFIAA

EKRGSNLEVELWLITAFHDKGSLTDYLKGNIITWNELCHVAETMSRGLSY

LHEDVPWCRGEGHKPSIAHRDFKSKNVLLKSDLTAVLADFGLAVRFEPGK

PPGDTHGQVGTRRYMAPEVLEGAINFQRDAFLRIDMYAMGLVLWELVSRC

KAADGPVDEYMLPFEEEIGQHPSLEELQEVVVHKKMRPTIKDHWLKHPGL

AQLCVTIEECWDHDAEARLSAGCVEERVSLIRRSVNGTTSDCLVSLVTSV

TNVDLPPKESSI
```

A protein comprising an extracellular domain of ActRIIB (ECD) may comprise amino acids 19-134 of SEQ ID NO: 1, or smaller portions, such as amino acids 20-134, 25-131 or any polypeptide comprising a portion of SEQ ID NO: 1 beginning at any of amino acids 19-29 and ending at any of amino acids 129-134. Each of the foregoing has been demonstrated to retain ligand binding activity. A protein comprising an extracellular domain of ActRIIB may comprise a polypeptide that is at least 80, 85, 90, 95, 96, 97, 98, 99 or 100% identical to any of the foregoing amino acid sequence portions of SEQ ID NO: 1. An ActRIIB-Fc fusion protein is any protein comprising any of the foregoing extracellular domains of ActRIIB and an Fc portion of an immunoglobulin (e.g., IgG1, IgG2, IgG4), optionally including an interposed linker between the ActRIIB portion and the Fc portion.

The nucleic acid sequence encoding human ActRIIB precursor protein is as follows (nucleotides 25-1560 of Genbank NM_001106.3):

```
                                          (SEQ ID NO: 2)
atgacggcgc cctgggtggc cctcgccctc ctctggggat

cgctgtgcgc cggctctggg cgtggggagg ctgagacacg

ggagtgcatc tactacaacg ccaactggga gctggagcgc

accaaccaga gcggcctgga gcgctgcgaa ggcgagcagg

acaagcggct gcactgctac gcctcctggc gcaacagctc

tggcaccatc gagctcgtga agaagggctg ctggctagat

gacttcaact gctacgatag gcaggagtgt gtggccactg

aggagaaccc ccaggtgtac ttctgctgct gtgaaggcaa

cttctgcaac gaacgcttca ctcatttgcc agaggctggg
```

-continued

```
ggcccggaag tcacgtacga gccacccccg acagccccca

ccctgctcac ggtgctggcc tactcactgc tgcccatcgg

gggcctttcc ctcatcgtcc tgctggcctt ttggatgtac

cggcatcgca agccccccta cggtcatgtg gacatccatg

aggaccctgg gcctccacca ccatcccctc tggtgggcct

gaagccactg cagctgctgg agatcaaggc tcgggggcgc

tttggctgtg tctggaaggc ccagctcatg aatgactttg

tagctgtcaa gatcttccca ctccaggaca agcagtcgtg

gcagagtgaa cgggagatct tcagcacacc tggcatgaag

cacgagaacc tgctacagtt cattgctgcc gagaagcgag

gctccaacct cgaagtagag ctgtggctca tcacggcctt

ccatgacaag ggctccctca cggattacct caaggggaac

atcatcacat ggaacgaact gtgtcatgta gcagagacga

tgtcacgagg cctctcatac ctgcatgagg atgtgccctg

gtgccgtggc gagggccaca agccgtctat tgcccacagg

gactttaaaa gtaagaatgt attgctgaag agcgacctca

cagccgtgct ggctgacttt ggcttggctg ttcgatttga

gccagggaaa cctccagggg acacccacgg acaggtaggc

acgagacggt acatggctcc tgaggtgctc gagggagcca

tcaacttcca gagagatgcc ttcctgcgca ttgacatgta

tgccatgggg ttggtgctgt gggagcttgt gtctcgctgc

aaggctgcag acggacccgt ggatgagtac atgctgccct

ttgaggaaga gattggccag caccccttcgt tggaggagct

gcaggaggtg gtggtgcaca agaagatgag gcccaccatt

aaagatcact ggttgaaaca cccgggcctg gcccagcttt

gtgtgaccat cgaggagtgc tgggaccatg atgcagaggc

tcgcttgtcc gcgggctgtg tggaggagcg ggtgtccctg

attcggaggt cggtcaacgg cactacctcg gactgtctcg

tttccctggt gacctctgtc accaatgtgg acctgccccc

taaagagtca agcatc
```

2. ActRIIB Binding Agents

The disclosure provides binding agents (such as antibodies) that specifically bind to ActRIIB or portions of ActRIIB, and methods for using such binding agents. The binding agents are useful to block or impair the binding of human ActRIIB to one or more ligand(s) and to interfere with its biological activity.

It will be understood by one of skill in the art that there is a high degree of sequence identity between the orthologs of ActRIIB. For example, a murine ortholog of human ActRIIB has been described (NCBI Ref. Seq.: NP_031423) that differs by only one amino acid substitution in the mature ActRIIB extracellular domain (119 amino acids). Accordingly, agents binding to human ActRIIB will be expected to bind to murine ActRIIB in cases where the recognition site of the binding agent, e.g., an antibody binding site such as an epitope, is highly conserved and in particular nearly or completely identical to the human sequence. Thus, when the term "specific binding to ActRIIB" is used, it is understood to include binding to multiple species of ActRIIB where the sequences between species are conserved.

Given the known structure of ActRIIB and the highly characterized ligand binding interface (see, e.g., Weber et al. 2007, BMC Structural Biology 7:6; Thompson et al. 2003 EMBO J. 22:1555-1566; WO 2006/012627), it is understood that neutralizing anti-ActRIIB antibodies will bind to amino acids within one or more of the following strings of amino acids of ActRIIB as follows (numbering is relative to SEQ ID NO: 1): amino acids 77-83 of SEQ ID NO: 1, amino acids 60-64 of SEQ ID NO: 1, 73-74 of SEQ ID NO: 1, amino acids 73-83 of SEQ ID NO: 1, amino acids 98-101 of SEQ ID NO: 1; amino acids 35-39 of SEQ ID NO:1 and/or amino acids 52-55 of SEQ ID NO: 1.

Examples of binding agents according to the invention include the antibody 17G05 (Ab-17G05) and the corresponding Fab-17G05. As used herein, Ab-17G05 comprises the polypeptides expressed by the nucleotides shown in SEQ ID NOs: 17 and 18.

Binding agents of the invention are typically antibodies or fragments thereof, as defined herein. The term "antibody" refers to an intact antibody, or a binding fragment thereof. An antibody may comprise a complete antibody molecule (including polyclonal, monoclonal, chimeric, humanized, or human versions having full-length heavy and/or light chains), or comprise an antigen-binding fragment thereof. Antibody fragments include $F(ab')_2$, Fab, Fab', Fv, Fc, and Fd fragments, and can be incorporated into single-domain antibodies, single-chain antibodies, maxibodies, minibodies, intrabodies, diabodies, triabodies, tetrabodies, v-NAR and bis-scFv (See e.g., Hollinger and Hudson, 2005, Nature Biotechnology, 23, 9, 1 126-1136). Antibody-like polypeptides are also disclosed in U.S. Pat. No. 6,703,199 ["Artificial Antibody Polypeptides", assigned to Research Corp Technologies], including fibronectin polypeptide monobodies. Other antibody-like polypeptides are disclosed in U.S. patent publication 2005/0238646, which are single-chain polypeptides. As used herein, the isolated antibody or an antigen-binding fragment thereof may be a polyclonal antibody, a monoclonal antibody, a humanized antibody, a human antibody, a chimeric antibody, or the like. In each of these types of binding agents, it is generally expected that one would insert one or more CDRs from the antibodies disclosed herein to produce an alternative ActRIIB binding agent.

An antibody according to the present invention may belong to any immunoglobin class, for example IgG, IgE, IgM, IgD, or IgA. It may be obtained from or derived from an animal, for example, birds (e.g., chicken) and mammals, which include but are not limited to a mouse, rat, hamster, rabbit, cow, horse, sheep, goat, camel, human, or other primate. The antibody may be an internalizing antibody. Within the human IgG class, classes IgG1, IgG2 and IgG4 are particularly useful. An anti-ActRIIB antibody of the IgG2 or IgG4 class may be particularly useful as a therapeutic as these classes will diminish the action of the immune system against cells to which the anti-ActRIIB antibody binds.

Antigen binding fragments derived from an antibody can be obtained, for example, by proteolytic hydrolysis of the antibody, for example, pepsin or papain digestion of whole antibodies according to conventional methods. By way of example, antibody fragments can be produced by enzymatic cleavage of antibodies with pepsin to provide a 5S fragment termed $F(ab')_2$. This fragment can be further cleaved using a thiol reducing agent to produce 3.5S Fab monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoff et al., Arch. Biochem. Biophys. 89:230, 1960; Porter, Biochem. J. 73:119, 1959; Edelman et al., in Methods in Enzymology 1:422 (Academic Press 1967); and by Andrews, S. M. and Titus, J. A. in Current Protocols in Immunology (Coligan J. E., et al., eds), John Wiley & Sons, New York (2003), pages 2.8.1-2.8.10 and 2.10A.1-2.10A.5. Other methods for cleaving antibodies, such as separating heavy chains to form monovalent light-heavy chain fragments (Fd), further cleaving of fragments, or other enzymatic, chemical, or genetic techniques may also be used, so long as the fragments bind to the antigen that is recognized by the intact antibody.

An antibody fragment may also be any synthetic or genetically engineered protein. For example, antibody fragments include isolated fragments consisting of the light chain variable region, "Fv" fragments consisting of the variable regions of the heavy and light chains, recombinant single-chain polypeptide molecules in which light and heavy variable regions are connected by a peptide linker (scFv proteins).

Another form of an antibody fragment is a peptide comprising one or more complementarity determining regions (CDRs) of an antibody. CDRs (also termed "minimal recognition units", or "hypervariable regions") can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., Methods: A Companion to Methods in Enzymology 2:106, 1991; Courtenay-Luck, "Genetic Manipulation of Monoclonal Antibodies," in Monoclonal Antibodies. Production, Engineering and Clinical Application, Ritter et al. (eds.), page 166 (Cambridge University Press 1995); and Ward et al., "Genetic Manipulation and Expression of Antibodies," in Monoclonal Antibodies: Principles and Applications, Birch et al., (eds.), page 137 (Wiley-Liss, Inc. 1995)).

Thus, in one embodiment, the binding agent comprises at least one CDR as described herein. The binding agent may comprise at least two, three, four, five or six CDRs, as described herein. The binding agent further may comprise at least one variable region domain of an antibody described herein. The variable region domain may be of any size or amino acid composition and will generally comprise at least one CDR sequence responsible for binding to human ActRIIB, for example CDR-H1, CDR-H2, CDR-H3, and/or the light chain CDRs specifically described herein and which are adjacent to or in frame with one or more framework sequences. In general terms, the variable (V) region domain may be any suitable arrangement of immunoglobulin heavy (VH) and/or light (VL) chain variable domains. Thus, for example, the V region domain may be monomeric and be a VH or VL domain, which is capable of independently binding human ActRIIB with an affinity at least equal to $1\times10^{-7}$ M or less as described below. Alternatively, the V region domain may be dimeric and contain VH-VH, VH-VL, or VL-VL dimers. The V region dimer comprises at least one VH and at least one VL chain that may be non-covalently associated (hereinafter referred to as FV). If desired, the chains may be covalently coupled either directly, for example via a disulfide bond between the two variable domains, or through a linker, for example a peptide linker, to form a single chain Fv (scFV).

The variable region domain may be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain may be covalently attached at a C-terminal amino acid to at least one other antibody domain or a fragment thereof. Thus, for example, a VH domain that is present in the variable region domain may be linked to an immunoglobulin CH1 domain, or a fragment thereof. Similarly a VL domain may be linked to a CK domain or a fragment thereof. In this way, for example, the antibody may be a Fab fragment wherein the antigen binding domain contains associated VH and VL domains covalently linked at their C-termini to a CH1 and CK domain, respectively. The CH1 domain may be extended with further amino acids, for example to provide a hinge region or a portion of a hinge region domain as found in a Fab fragment, or to provide further domains, such as antibody CH2 and CH3 domains.

As described herein, binding agents may comprise at least one of these CDRs. For example, one or more CDRs may be incorporated into known antibody framework regions (IgG1, IgG2, etc.), or conjugated to a suitable vehicle to enhance the half-life thereof. Suitable vehicles include, but are not limited to Fc, polyethylene glycol (PEG), albumin, transferrin, and the like. These and other suitable vehicles are known in the art. Such conjugated CDR peptides may be in monomeric, dimeric, tetrameric, or other form. In one embodiment, one or more water-soluble polymer is bonded at one or more specific position, for example at the amino terminus, of a binding agent.

In certain embodiments, a binding agent comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative binding agent comprises one or more of monomethoxy-polyethylene glycol, dextran, cellulose, or other carbohydrate-based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymers is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

Antibodies according to the invention may be obtained by conventional immunization and cell fusion procedures as described herein and known in the art. Monoclonal antibodies of the invention may be generated using a variety of known techniques. In general, monoclonal antibodies that bind to specific antigens may be obtained by methods known to those skilled in the art (see, for example, Kohler et al., Nature 256:495, 1975; Coligan et al. (eds.), Current Protocols in Immunology, 1:2.5.12.6.7 (John Wiley & Sons 1991); U.S. Pat. Nos. RE 32,011, 4,902,614, 4,543,439, and 4,411,993; Monoclonal Antibodies, Hybridomas: A New Dimension in Biological Analyses, Plenum Press, Kennett, McKearn, and Bechtol (eds.) (1980); and Antibodies: A Laboratory Manual, Harlow and Lane (eds.), Cold Spring Harbor Laboratory Press (1988); Picksley et al., "Production of monoclonal antibodies against proteins expressed in *E. coli*," in DNA Cloning 2: Expression Systems, 2nd Edition, Glover et al. (eds.), page 93 (Oxford University Press 1995)). Antibody fragments may be derived therefrom using any suitable standard technique such as proteolytic digestion, or optionally, by proteolytic digestion (for example, using papain or pepsin) followed by mild reduction of disulfide bonds and alkylation. Alternatively, such fragments may also be generated by recombinant genetic engineering techniques as described herein.

Monoclonal antibodies can be obtained by injecting an animal, for example, a rat, hamster, rabbit, or mouse, with an immunogen comprising human ActRIIB of SEQ ID NO: 1, or a fragment thereof, according to methods known in the art and described herein. A polypeptide comprising amino acids 19-134 or 20-134 of SEQ ID NO: 1 is particularly useful for generating antibodies that bind to the extracellular domain of ActRIIB, which includes the ligand binding portion. The presence of specific antibody production may be monitored after the initial injection and/or after a booster injection by obtaining a serum sample and detecting the presence of an antibody that binds to human ActRIIB or peptide using any one of several immunodetection methods known in the art and described herein. From animals producing the desired antibodies, lymphoid cells, most commonly cells from the spleen or lymph node, are removed to obtain B-lymphocytes. The B lymphocytes are then fused with a drug-sensitized myeloma cell fusion partner, preferably one that is syngeneic with the immunized animal and that optionally has other desirable properties (e.g., inability to express endogenous Ig gene products, e.g., P3X63-Ag 8.653 (ATCC No. CRL 1580); NSO, SP20) to produce hybridomas, which are immortal eukaryotic cell lines. The lymphoid (e.g., spleen) cells and the myeloma cells may be combined for a few minutes with a membrane fusion-promoting agent, such as polyethylene glycol or a nonionic detergent, and then plated at low density on a selective medium that supports the growth of hybridoma cells but not unfused myeloma cells. A preferred selection media is HAT (hypoxanthine, aminopterin, thymidine). After a sufficient time, usually about one to two weeks, colonies of cells are observed. Single colonies are isolated, and antibodies produced by the cells may be tested for binding activity to human ActRIIB, using any one of a variety of immunoassays known in the art and described herein. The hybridomas are cloned (e.g., by limited dilution cloning or by soft agar plaque isolation) and positive clones that produce an antibody specific to ActRIIB are selected and cultured. The monoclonal antibodies from the hybridoma cultures may be isolated from the supernatants of hybridoma cultures. An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in Methods in Molecular Biology, Vol. 10, pages 79-104 (The Humana Press, Inc. 1992)). Monoclonal antibodies may be purified by affinity chromatography using an appropriate ligand whose selection is based on particular properties of the antibody (e.g., heavy-or light-chain isotype, binding specificity, etc.). Examples of a suitable ligand, immobilized on a solid support, include Protein A, Protein G, an anti-constant region (light chain or heavy chain) antibody, an anti-idiotype antibody, or fragment or variant thereof.

It will be appreciated by one of skill in the art that a binding agent of the present invention may have at least one amino acid substitution, providing that the binding agent retains binding specificity. Therefore, modifications to the binding agent structures are encompassed within the scope of the invention. These may include amino acid substitutions, which may be conservative or non-conservative and that do not destroy the ActRIIB binding capability of a binding agent. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. A conservative amino acid substitution may also involve a substitution of a native amino acid residue with a normative residue such that there is little or no effect on the polarity or charge of the amino acid residue at that position.

Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

Conservative Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Arg; Asn; Gln; Lys | Arg |
| Ile (I) | Leu; Val; Met; Ala; Phe; Norleucine | Leu |
| Leu (L) | Ile; Norleucine; Val; Met; Ala; Phe | Ile |
| Lys (K) | Arg; Gln; Asn | Arg |
| Met (M) | Leu; Phe; Ile | Leu |
| Phe (F) | Tyr; Trp; Leu; Val; Ile; Ala | Tyr |
| Pro (P) | Ala | Ala |
| Ser (S) | Thr | Thr |
| Thr (T) | Ser; Val | Ser |
| Trp (W) | Tyr; Phe | Tyr |
| Tyr (Y) | Phe; Trp; Thr; Ser | Phe |
| Val (V) | Leu; Ile; Norleucine; Met; Phe; Ala | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Met, Ala, Val, Leu, Ile, Norleucine;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro; and (6) aromatic: Trp, Tyr, Phe.

Non-conservative substitutions may involve the exchange of a member of one class of amino acids or amino acid mimetics for a member from another class with different physical properties (e.g. size, polarity, hydrophobicity, charge). Such substituted residues may be introduced into regions of the human antibody that are homologous with non-human antibodies, or into the nonhomologous regions of the molecule.

Moreover, one skilled in the art may generate test variants containing a single amino acid substitution at each desired amino acid residue. The variants can then be screened using activity assays as described herein. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2): 211-222 (1974); Chou et al., Adv. Enzymol. Relat. Areas MoI. Biol., 47: 45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or sequence similarity greater than 40% often have similar structural topologies. The recent growth of the protein structural database (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., Curr. Opin. Struct. Biol., 7(3):377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci., 84(13):4355-4358 (1987)), and "evolutionary linkage" (See Holm, supra (1999), and Brenner, supra (1997)).

It will be understood by one skilled in the art that some proteins, such as antibodies, may undergo a variety of posttranslational modifications during expression and secretion from host cells. The type and extent of these modifications often depends on the host cell line used to express the protein as well as the culture conditions. Such modifications may include variations in glycosylation, methionine or tryptophan oxidation, diketopiperizine formation, aspartate isomerization and asparagine deamidation. A frequent modification is the loss of a carboxy-terminal basic residue (such as lysine or arginine) due to the action of carboxypeptidases (as described in Harris, RJ. Journal of Chromatography 705:129-134, 1995). Once the proteins have been expressed and processed they are in a 'mature' form. Thus it is understood that the invention includes mature antibodies that result from expression of the DNAs of the invention.

In certain embodiments, variants of binding agents include glycosylation variants wherein the number and/or type of glycosylation site has been altered compared to the amino acid sequences of a parent polypeptide. In certain embodiments, variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Amino acid substitutions (whether conservative or non-conservative) can be determined by those skilled in the art at the time such substitutions are desired. In certain embodiments, amino acid substitutions can be used to identify important residues of antibodies to ActRIIB, or to increase or decrease the affinity of the antibodies to ActRIIB described herein.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W.H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

In certain embodiments, binding agents of the invention may be chemically bonded with polymers, lipids, or other moieties.

The binding agents may comprise at least one of the CDRs described herein incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids (e.g., CDRs, a variable region, etc.) that bind to an antigen in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria, or virus.

Typically the biocompatible framework structures are based on protein scaffolds or skeletons other than immunoglobulin domains. For example, those based on fibronectin, ankyrin, lipocalin, neocarzinostain, cytochrome b, CPl zinc finger, PST1, coiled coil, LACI-Dl, Z domain and tendramisat domains may be used (See e.g., Nygren and Uhlen, 1997, Current Opinion in Structural Biology, 7, 463-469).

In preferred embodiments, it will be appreciated that the binding agents of the invention include humanized antibodies, which can be produced using techniques known to those skilled in the art (Zhang, W., et al., Molecular Immunology. 42(12): 1445-1451, 2005; Hwang W. et al., Methods. 36(1): 35-42, 2005; Dall'Acqua W F, et al., Methods 36(1):43-60, 2005; and Clark, M., Immunology Today. 21(8):397-402, 2000).

An antibody of the present invention may also be a human monoclonal antibody. Human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B cells, fusion of spleen cells from immunized transgenic mice carrying inserted human immunoglobulin genes, isolation from human immunoglobulin V region phage libraries, or other procedures as known in the art and based on the disclosure herein. For example, human monoclonal antibodies may be obtained from transgenic mice that have been engineered to produce specific human antibodies in response to antigenic challenge. Methods for obtaining human antibodies from transgenic mice are described, for example, by Green et al., Nature Genet. 7:13, 1994; Lonberg et al., Nature 368:856, 1994; Taylor et al., Int. Immun. 6:579, 1994; U.S. Pat. No. 5,877,397; Bruggemann et al., 1997 Curr. Opin. Biotechnol. 8:455-58; Jakobovits et al., 1995 Ann. N. Y Acad. Sci. 764:525-35. In this technique, elements of the human heavy-and light-chain locus are introduced into strains of mice derived from embryonic stem cell lines that contain targeted disruptions of the endogenous heavy-chain and light-chain loci (see also Bruggemann et al., Curr. Opin. Biotechnol. 8:455-58 (1997)). For example, human immunoglobulin transgenes may be mini-gene constructs, or transloci on yeast artificial chromosomes, which undergo B cell-specific DNA rearrangement and hypermutation in the mouse lymphoid tissue. Human monoclonal antibodies may be obtained by immunizing the transgenic mice, which may then produce human antibodies specific for ActRIIB. Lymphoid cells of the immunized transgenic mice can be used to produce human antibody-secreting hybridomas according to the methods described herein. Polyclonal sera containing human antibodies may also be obtained from the blood of the immunized animals.

Another method for generating human antibodies of the invention includes immortalizing human peripheral blood cells by EBV transformation. See, e.g., U.S. Pat. No. 4,464,456. Such an immortalized B cell line (or lymphoblastoid cell line) producing a monoclonal antibody that specifically binds to ActRIIB can be identified by immunodetection methods as provided herein, for example, an ELISA, and then isolated by standard cloning techniques. The stability of the lymphoblastoid cell line producing an anti-ActRIIB antibody may be improved by fusing the transformed cell line with a murine myeloma to produce a mouse-human hybrid cell line according to methods known in the art (see, e.g., Glasky et al., Hybridoma 8:377-89 (1989)). Still another method to generate human monoclonal antibodies is in vitro immunization, which includes priming human splenic B cells with human ActRIIB, followed by fusion of primed B cells with a heterohybrid fusion partner. See, e.g., Boerner et al., 1991, J. Immunol. 147:86-95.

In certain embodiments, a B cell that is producing an anti-human ActRIIB antibody is selected and the light chain and heavy chain variable regions are cloned from the B cell according to molecular biology techniques known in the art (WO 92/02551; U.S. Pat. No. 5,627,052; Babcook et al., Proc. Natl. Acad. Sci. USA 93:7843-48 (1996)) and described herein. B cells from an immunized animal may be isolated from the spleen, lymph node, or peripheral blood sample by selecting a cell that is producing an antibody that specifically binds to ActRIIB. B cells may also be isolated from humans, for example, from a peripheral blood sample. Methods for detecting single B cells that are producing an antibody with the desired specificity are well known in the art, for example, by plaque formation, fluorescence-activated cell sorting, in vitro stimulation followed by detection of specific antibody, and the like. Methods for selection of specific antibody-producing B cells include, for example, preparing a single cell suspension of B cells in soft agar that contains human ActRIIB. Binding of the specific antibody produced by the B cell to the antigen results in the formation of a complex, which may be visible as an immunoprecipitate. After the B cells producing the desired antibody are selected, the specific antibody genes may be cloned by isolating and amplifying DNA or mRNA according to methods known in the art and described herein.

Additionally, one skilled in the art will recognize that suitable binding agents include portions of these antibodies, such as one or more of CDR-H1, CDR-H2, CDR-H3, CDR-L1, CDR-L2 and CDR-L3, as specifically disclosed herein. At least one of the regions of CDR-H1, CDR-H2, CDR-H3, CDR-L1, CDR-L2 and CDR-L3 may have at least one amino acid substitution, provided that the binding agent retains the binding specificity of the non-substituted CDR. CDRs may be altered to increase or decrease length as well, and thus changes that are characterized as substitutions, insertions and deletions are all contemplated. The non-CDR portion of the binding agent may be a non-protein molecule, wherein the binding agent cross-blocks the binding of an antibody disclosed herein to ActRIIB and/or neutralizes ActRIIB. The non-CDR portion of the binding agent may be composed of amino acids, wherein the binding agent is a recombinant binding protein or a synthetic peptide, and the recombinant binding protein cross-blocks the binding of an antibody disclosed herein to ActRIIB and/or neutralizes ActRIIB. The non-CDR portion of the binding agent may be composed of amino acids, wherein the binding agent is a recombinant binding protein, and the recombinant binding protein exhibits a similar binding pattern to human ActRIIB peptides in the human ActRIIB peptide epitope competition binding assay (described hereinbelow) as that exhibited by antibody Ab-17G05, and/or neutralizes ActRIIB.

In one embodiment, it is contemplated that one can use the antibody heavy chain as 'bait' in a library screen where the library is composed of human antibody light chains, to identify complementing human light chains where the reconstituted antibody binds to ActRIIB. In this embodiment, the heavy chain is from an antibody specific to ActRIIB and is mouse, chimeric, or humanized.

Where an antibody comprises one or more of CDR-H1, CDR-H2, CDR-H3, CDR-L1, CDR-L2, and CDR-L3, as described above, it may be obtained by expression from a host cell containing DNA coding for these sequences. A DNA coding for each CDR sequence may be determined on the basis of the amino acid sequence of the CDR and synthesized together with any desired antibody variable region framework and constant region DNA sequences using oligonucleotide synthesis techniques, site-directed mutagenesis and polymerase chain reaction (PCR) techniques as appropriate. DNA coding for variable region frameworks and constant regions is widely available to those skilled in the art from genetic sequences databases such as GenBank®.

Once synthesized, the DNA encoding an antibody of the invention or fragment thereof may be propagated and expressed according to any of a variety of well-known procedures for nucleic acid excision, ligation, transformation, and transfection using any number of known expression vectors. Thus, in certain embodiments expression of an antibody fragment may be preferred in a prokaryotic host, such as *Escherichia coli* (see, e.g., Pluckthun et al., 1989 Methods Enzymol. 178:497-515). In certain other embodiments, expression of the antibody or a fragment thereof may be preferred in a eukaryotic host cell, including yeast (e.g., *Saccharomyces cerevisiae, Schizosaccharomyces pombe*, and *Pichia pastoris*), animal cells (including mammalian cells) or plant cells. Examples of suitable animal cells include, but are not limited to, myeloma (such as a mouse NSO line), COS, CHO, or hybridoma cells. Examples of plant cells include tobacco, corn, soybean, and rice cells.

One or more replicable expression vectors containing DNA encoding an antibody variable and/or constant region may be prepared and used to transform an appropriate cell line, for example, a non-producing myeloma cell line, such as a mouse NSO line or a bacteria, such as *E. coli*, in which production of the antibody will occur. To obtain efficient transcription and translation, the DNA sequence in each vector should include appropriate regulatory sequences, particularly a promoter and leader sequence operatively linked to the variable domain sequence. Particular methods for producing antibodies in this way are generally well-known and routinely used. For example, basic molecular biology procedures are described by Maniatis et al. (Molecular Cloning, A Laboratory Manual, 2nd ed., Cold Spring Harbor Laboratory, New York, 1989; see also Maniatis et al, 3rd ed., Cold Spring Harbor Laboratory, New York, (2001)). DNA sequencing can be performed as described in Sanger et al. (PNAS 74:5463, (1977)) and the Amersham International pic sequencing handbook, and site directed mutagenesis can be carried out according to methods known in the art (Kramer et al., Nucleic Acids Res. 12:9441, (1984); Kunkel Proc. Natl. Acad. Sci. USA 82:488-92 (1985); Kunkel et al., Methods in Enzymol. 154:367-82 (1987); the Anglian Biotechnology Ltd handbook). Additionally, numerous publications describe techniques suitable for the preparation of antibodies by manipulation of DNA, creation of expression vectors, and transformation and culture of appropriate cells (Mountain A and Adair, J R in Biotechnology and Genetic Engineering Reviews (ed. Tombs, M P, 10, Chapter 1, 1992, Intercept, Andover, UK); "Current Protocols in Molecular Biology", 1999, F. M. Ausubel (ed.), Wiley Interscience, New York).

Where it is desired to improve the affinity of antibodies according to the invention containing one or more of the above-mentioned CDRs, improved antibodies can be obtained by a number of affinity maturation protocols including maintaining the CDRs (Yang et al., J. MoI. Biol., 254, 392-403, 1995), chain shuffling (Marks et al., Bio/Technology, 10, 779-783, 1992), use of mutation strains of *E. coli*. (Low et al., J. MoI. Biol., 250, 350-368, 1996), DNA shuffling (Patten et al., Curr. Opin. Biotechnol., 8, 724-733, 1997), phage display (Thompson et al., J. MoI. Biol., 256, 7-88, 1996) and sexual PCR (Crameri, et al., Nature, 391, 288-291, 1998). All of these methods of affinity maturation are discussed by Vaughan et al. (Nature Biotechnology, 16, 535-539, 1998).

An additional method for obtaining or maturing antibodies of the invention is by phage display. See, e.g., Winter et al., 1994 Annu. Rev. Immunol. 12:433-55; Burton et al., 1994 Adv. Immunol. 57:191-280. See also the methodology described in the Examples. Combinatorial libraries of human or murine immunoglobulin variable-region genes may be created in phage vectors that can be screened to select Ig fragments (Fab, Fv, sFv, or multimers thereof) that bind specifically to ActRIIB or variant or fragment thereof. See, e.g., U.S. Pat. No. 5,223,409; Huse et al., 1989 Science 246:1275-81; Sastry et al., Proc. Natl. Acad. Sci. USA 86:5728-32 (1989); Alting-Mees et al., Strategies in Molecular Biology 3:1-9 (1990); Kang et al., 1991 Proc. Natl. Acad. Sci. USA 88:4363-66; Hoogenboom et al., 1992 J. Molec. Biol. 227:381-388; Schlebusch et al., 1997 Hybridoma 16:47-52 and references cited therein; and Hoet et al., 2005, Nat Biotechnol 23:344-348. For example, a library containing a plurality of polynucleotide sequences encoding Ig variable region fragments may be inserted into the genome of a filamentous bacteriophage, such as M 13 or a variant thereof, in frame with the sequence encoding a phage coat protein. A fusion protein may be a fusion of the coat protein with the light chain variable-region domain and/or with the heavy chain variable-region domain. According to certain embodiments, immunoglobulin Fab fragments may also be displayed on a phage particle (see, e.g., U.S. Pat. No. 5,698,426).

Heavy and light chain immunoglobulin cDNA expression libraries may also be prepared in lambda phage, for example, using lambda ImmunoZap™ (H) and lambda ImmunoZap™ (L) vectors (Stratagene, La Jolla, Calif.). Briefly, mRNA is isolated from a B cell population, and used to create heavy and light chain immunoglobulin cDNA expression libraries in the lambda ImmunoZap(H) and lambda ImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid that allows high level expression of monoclonal antibody fragments from *E. coli.*

In one embodiment in a hybridoma, the variable regions of a gene expressing a monoclonal antibody of interest are amplified using nucleotide primers. These primers may be synthesized by one of ordinary skill in the art, or may be purchased from commercially available sources. (See, e.g., Stratagene (La Jolla, Calif.), which sells primers for mouse and human variable regions including, among others, primers for VHa, VHb, VHc, VHd, CHI, VL and CL regions.) These primers may be used to amplify heavy or light chain variable regions, which may then be inserted into vectors such as ImmunoZAP™ H or ImmunoZAP™ (Stratagene), respectively. These vectors may then be introduced into *E. coli*, yeast, or mammalian-based systems for expression. Large amounts of a single-chain protein containing a fusion of the VH and VL domains may be produced using these methods (see Bird et al., Science 242:423-426, 1988).

Once cells producing antibodies according to the invention have been obtained using any of the above-described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described previously to generate other antibodies according to the invention.

Preferably the binding agents bind specifically to ActRIIB. As with all binding agents and binding assays, one of skill in this art recognizes that the various moieties to which a binding agent should not detectably bind in order to be therapeutically effective and suitable would be exhaustive and impractical to list. Therefore, for a binding agent disclosed herein, the term "specifically binds" refers to the ability of a binding agent to bind to ActRIIB, preferably human ActRIIB, with greater affinity than it binds to an unrelated control protein. Preferably the control protein is hen egg white lysozyme. Preferably the binding agents bind to ActRIIB with an affinity that is at least, 50, 100, 250, 500, 1000, or 10,000 times greater than the affinity for a control protein. A binding agent may have a binding affinity for human ActRIIB of less than or equal to $1\times10^{-7}$ M, less than or equal to $1\times10^{-8}$ M, less than or equal to $1\times10^{-9}$ M, less than or equal to $1\times10^{-10}$ M, less than or equal to $1\times10^{-11}$ M, or less than or equal to $1\times10^{-12}$ M. Antibodies having improved affinity may be generated by any of a variety of known maturation techniques, such as those described above. Affinity may be assessed at different temperatures, using any of the techniques described herein. Temperatures of 20 deg. C., 25 deg. C. or 37 deg. C. may be used.

Affinity may be determined by an affinity ELISA assay. In certain embodiments, affinity may be determined by a BIACORE™ assay. In certain embodiments, affinity may be determined by a kinetic method. In certain embodiments, affinity may be determined by an equilibrium/solution method. Such methods are described in further detail herein or known in the art.

The affinity of a binding agent such as an antibody or binding partner, as well as the extent to which a binding agent (such as an antibody) inhibits binding, can be determined by one of ordinary skill in the art using conventional techniques, for example by surface plasmon resonance (SPR; BIACORE™, Biosensor, Piscataway, N.J.) or according to methods described by Scatchard et al. (Ann. N.Y. Acad. Sci. 51:660-672 (1949)). For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al., Cancer Res. 53:2560-65 (1993)).

An oligopeptide or polypeptide is within the scope of the invention if it comprises an amino acid sequence that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to at least one of the CDRs depicted in the Examples (SEQ ID NOs: 19-42); and/or to a CDR of an ActRIIB binding agent that cross-blocks the binding of Ab-17G05 to ActRIIB, and/or is cross-blocked from binding to ActRIIB by Ab-17G05; and/or to a CDR of an ActRIIB binding agent wherein the binding agent can block the effect of ActRIIB in a cell-based assay (i.e. an ActRIIB neutralizing binding agent).

Examples of ActRIIB binding agent polypeptides and antibodies that are within the scope of the invention are those that have amino acid sequences that are at least 85%, 86%, 87%, 88%, 89%, 90%, 91%, 92%, 93%, 94%, 95%, 96%, 97%, 98% or 99% identical to a variable region of Ab-17G05 (SEQ ID NOs: 15 and 16), and cross-block the binding of Ab-17G05 to ActRIIB, and/or are cross-blocked from binding to ActRIIB by Ab-17G05; and/or can block the inhibitory effect of ActRIIB in a cell-based assay (i.e. an ActRIIB neutralizing binding agent).

Examples of polynucleotides encoding ActRIIB binding agents that are within the scope of the invention are those that have polynucleotide sequences that are at least 85%, 86%, 87%, 88%, 89%, 90%, 91%, 92%, 93%, 94%, 95%, 96%, 97%, 98% or 99% identical to a polynucleotide encoding a variable region of Ab-17G05 (SEQ ID NOs: 17 and 18), and wherein the encoded ActRIIB binding agents cross-block the binding of Ab-17G05 to ActRIIB, and/or are cross-blocked from binding to ActRIIB by Ab-17G05; and/or can block the inhibitory effect of ActRIIB in a cell-based assay (i.e. an ActRIIB neutralizing binding agent).

ActRIIB binding agents of the present invention preferably modulate ActRIIB function in the cell-based assay described herein and/or the in vivo assay described herein and/or cross-block the binding of antibody Ab-17G05 described in this application and/or are cross-blocked from binding ActRIIB by the antibody Ab-17G05 described in this application. Accordingly, such binding agents can be identified using the assays described herein.

In certain embodiments, binding agents are generated by first identifying antibodies that neutralize ActRIIB in the cell-based and/or in vivo assays described herein and/or cross-block the antibody Ab-17G05 described in this application and/or are cross-blocked from binding ActRIIB by antibody Ab-17G05 described in this application. The CDR regions from these antibodies are then used to insert into appropriate biocompatible frameworks to generate ActRIIB binding agents. The non-CDR portion of the binding agent may be composed of amino acids, or may be a nonprotein molecule. The assays described herein allow the characterization of binding agents. Preferably the binding agents of the present invention are antibodies as defined herein.

In the methods described herein to generate antibodies according to the invention, including the manipulation of the specific Ab-17G05 CDRs into new frameworks and/or constant regions, appropriate assays are available to select the desired antibodies or binding agents (i.e. assays for determining binding affinity to ActRIIB; cross-blocking assays such as the BIACORE™-based human ActRIIB peptide competition binding assays described in Example 2 below; A204 cell-based assay; in vivo assays).

The terms "cross-block", "cross-blocked" and "cross-blocking" are used interchangeably herein to mean the ability of an antibody or other binding agent to interfere with the binding of other antibodies or binding agents to ActRIIB.

The extent to which an antibody or other binding agent is able to interfere with the binding of another to ActRIIB, and therefore whether it can be said to cross-block according to the invention, can be determined using competition binding assays. One particularly suitable quantitative assay uses a BIACORE™ instrument which can measure the extent of interactions using surface plasmon resonance technology. Example 2 provides methods for conducting a BIACORE™ based cross-blocking assays. Another suitable quantitative cross-blocking assay uses an ELISA-based approach to measure competition between antibodies or other binding agents in terms of their binding to ActRIIB.

The following generally describes a suitable BIACORE™ assay for determining whether an antibody or other binding agent cross-blocks or is capable of cross-blocking according to the invention. For convenience, reference is made to two antibodies, but it will be appreciated that the assay can be used with any of the ActRIIB binding agents described herein. The BIACORE™ instrument (for example the BIACORE™ 3000) is operated according to the manufacturer's recommendations.

Thus, in one cross-blocking assay, ActRIIB-mFc fusion protein is captured on a CM5 BIACORE™ chip by previously attached anti-mFc IgG to generate an ActRIIB-coated surface. Typically 200-800 resonance units of ActRIIB-mFc (dimeric) would be coupled to the chip (an amount that gives easily measurable levels of binding but that is readily saturable by the concentrations of test reagent being used).

The two antibodies (termed A* and B*) to be assessed for their ability to cross-block each other are mixed at a one to one molar ratio of binding sites in a suitable buffer to create the test mixture. When calculating the concentrations on a binding site basis the molecular weight of an antibody is assumed to be the total molecular weight of the antibody divided by the number of ActRIIB binding sites on that antibody.

The concentration of each antibody in the test mix should be high enough to readily saturate the binding sites for that antibody on the ActRIIB-mFc molecules captured on the BIACORE™ chip. The antibodies in the mixture are at the same molar concentration (on a binding basis) and that concentration would typically be between 1.00 and 1.5 micromolar (on a binding site basis).

Separate solutions containing antibody A* alone and antibody B* alone are also prepared. Antibody A* and antibody B* in these solutions should be in the same buffer and at the same concentration as in the test mix.

The test mixture is passed over the ActRIIB-mFc-coated BIACORE™ chip and the total amount of binding recorded. The chip is then treated in such a way as to remove the bound antibodies without damaging the chip-bound ActRIIB-mFc. Typically, this is done by treating the chip with 30 mM HCl for 60 seconds.

The solution of antibody A* alone is then passed over the ActRIIB-mFc-coated surface and the amount of binding recorded. The chip is again treated to remove all of the bound antibody without damaging the chip-bound ActRIIB-mFc.

The solution of antibody B* alone is then passed over the ActRIIB-mFc-coated surface and the amount of binding recorded.

The maximum theoretical binding of the mixture of antibody A* and antibody B* is next calculated, and is the sum of the binding of each antibody when passed over the ActRIIB surface alone. If the actual recorded binding of the mixture is less than this theoretical maximum then the two antibodies are cross-blocking each other.

Thus, in general, a cross-blocking antibody or other binding agent according to the invention is one which will bind to ActRIIB in the above BIACORE™ cross-blocking assay such that during the assay and in the presence of a second antibody or other binding agent of the invention the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two antibodies or binding agents in combination.

The BIACORE™ assay described above is an assay used to determine if antibodies or other binding agents cross-block each other according to the invention. On rare occasions, particular antibodies or other binding agents may not bind to ActRIIB-mFc coupled via anti-mFc IgG to a CM5 BIACORE™ chip (this might occur when the relevant binding site on ActRIIB is masked or destroyed by ActRIIB linkage to mFc). In such cases, cross-blocking can be determined using a tagged version of ActRIIB, for example C-terminal His-tagged ActRIIB. In this particular format, an anti-His antibody would be coupled to the BIACORE™ chip and then the His-tagged ActRIIB would be passed over the surface of the chip and captured by the anti-His antibody. The cross-blocking analysis would be carried out essentially as described above, except that after each chip regeneration cycle, new His-tagged ActRIIB would be loaded back onto the surface coated with anti-His antibody. Moreover, various other tags and tag binding protein combinations that are known in the art could be used for such a cross-blocking analysis (e.g. HA tag with anti-HA antibodies; FLAG tag with anti-FLAG antibodies; biotin tag with streptavidin).

The following generally describes an ELISA assay for determining whether an anti-ActRIIB antibody or other ActRIIB binding agent cross-blocks or is capable of cross-blocking according to the invention. For convenience, reference is made to two antibodies, but it will be appreciated that the assay can be used with any of the ActRIIB binding agents described herein.

The general principle of the assay is to have an anti-ActRIIB antibody coated onto the wells of an ELISA plate. An excess amount of a second, potentially cross-blocking, anti-ActRIIB antibody is added in solution (i.e. not bound to the ELISA plate). A limited amount of ActRIIB (or alternatively ActRIIB-mFc) is then added to the wells. The coated antibody and the antibody in solution compete for binding of the limited number of ActRIIB (or ActRIIB-mFc) molecules. The plate is washed to remove ActRIIB that has not been bound by the coated antibody and to also remove the second, solution-phase antibody as well as any complexes formed between the second, solution-phase antibody and ActRIIB. The amount of bound ActRIIB is then measured using an appropriate ActRIIB detection reagent. An antibody in solution that is able to cross-block the coated antibody will be able to cause a decrease in the number of ActRIIB molecules that the coated antibody can bind relative to the number of ActRIIB molecules that the coated antibody can bind in the absence of the second, solution-phase antibody.

This assay is described here in more detail for Ab-17G05 and a theoretical antibody Ab-XX. In the instance where Ab-17G05 is chosen to be the immobilized antibody, it is coated onto the wells of the ELISA plate, after which the plates are blocked with a suitable blocking solution to minimize non-specific binding of reagents that are subsequently added. An excess amount of Ab-XX is then added to the ELISA plate such that the moles of Ab-XX ActRIIB binding sites per well are at least 10-fold higher than the moles of Ab-17G05 ActRIIB binding sites that were used, per well, during the coating of the ELISA plate.

ActRIIB is then added such that the moles of ActRIIB added per well are at least 25-fold lower than the moles of Ab-17G05 ActRIIB binding sites that were used for coating each well. Following a suitable incubation period the ELISA plate is washed and an ActRIIB detection reagent is added to measure the amount of ActRIIB specifically bound by the coated anti-ActRIIB antibody (in this case Ab-17G05). The background signal for the assay is defined as the signal obtained in wells with the coated antibody (in this case Ab-17G05), solution-phase antibody (in this case Ab-XX), ActRIIB buffer only (i.e. no ActRIIB) and ActRIIB detection reagents. The positive control signal for the assay is defined as the signal obtained in wells with the coated antibody (in this case Ab-17G05), solution-phase antibody buffer only (i.e. no solution-phase antibody), ActRIIB and ActRIIB detection reagents. The ELISA assay needs to be run in such a manner so as to have the positive control signal at least 3 times the background signal.

As a control for methodologic artifacts, the cross-blocking assay may be run in the format just described and also reversed, with Ab-XX as the coated antibody and Ab-17G05 as the solution-phase antibody.

A reporter gene assay in A204 cells may be used to determine the ability of anti-ActRIIB Fabs and recombinant antibodies to neutralize ActRIIB. This assay is based on a human rhabdomyosarcoma cell line transfected with a pGL3 (CAGA)12 reporter plasmid (Dennler et al, 1998, EMBO 17: 3091-3100) as well as a Renilla reporter plasmid (pRL-CMV) to control for transfection efficiency. The CAGA12 motif is present in TGF-beta responsive genes (PAI-1 gene), so this vector is of general use for factors signaling through Smad2 and Smad3. Since the A204 cell line expresses primarily ActRIIA rather than ActRIIB, it is not possible to directly test antibodies for potential ActRIIB neutralizing ability. Instead, this assay is designed to detect the ability of test articles to neutralize the inhibitory effect of the soluble fusion protein ActRIIB-Fc on activation of endogenous ActRIIA by ligands (such as activin A, myostatin or GDF11) that can bind with high affinity to both ActRIIA and ActRIIB. Thus, in this assay, ligand-mediated activation of ActRIIA will occur despite the presence of ActRIIB-Fc if the anti-ActRIIB Fab or antibody is neutralizing.

On the first day of the assay, A204 cells (ATCC HTB-82) are distributed in 48-well plates at $10^5$ cells per well. On the second day, a solution containing 10 μg pGL3(CAGA)12, 1 g pRLCMV, 30 μl Fugene 6 (Roche Diagnostics), and 970 μl OptiMEM (Invitrogen) is preincubated for 30 min, then added to McCoy's growth medium, which is applied to the plated cells (500 μl/well) for incubation overnight at room temperature. On the third day, medium is removed, and cells are incubated for 6 h at 37° C. with a mixture of ligands and inhibitors prepared as described below.

To evaluate the neutralizing potency of Fabs or recombinant antibodies, a serial dilution of the test article is made in a 48-well plate in a 200 μl volume of assay buffer (McCoy's medium+0.1% BSA). An equal volume of ActRIIB-Fc (200 μg/ml) in assay buffer is then added. The test solutions are incubated at 37° C. for 30 minutes, then 400 μl of GDF11 (10 ng/ml) or activin A (10 ng/ml) is added to all wells, and 350 μl of this mixture is added to each well of the 48-well plate of A204 cells. Each concentration of Fab or antibody is tested in duplicate. The final concentration of ActRIIB-Fc is 50 ng/ml (which is the IC50 for this inhibitor of activin A signaling when the final concentration of activin A is 5 ng/ml). After incubation with test solutions for 6 h, cells are rinsed with phosphate-buffered saline containing 0.1% BSA, then lysed with passive lysis buffer (Promega E1941) and stored overnight at −70° C. On the fourth and final day, plates are warmed to room temperature with gentle shaking. Cell lysates are transferred in duplicate to a chemoluminescence plate (96-well) and analyzed in a luminometer with reagents from a Dual-Luciferase Reporter Assay system (Promega E1980) to determine normalized luciferase activity.

Antibodies disclosed herein bind to regions of human ActRIIB which are important for the in vivo activity of the protein, thereby inhibiting the activity of ActRIIB. Ab-17G05 binds to an epitope within the sequence of amino acids 20-134 of SEQ ID NO: 1. Binding of an antibody to ActRIIB can be correlated with changes in biomarkers associated with ActRIIB-mediated signaling, for example, serum FSH levels, bone density, muscle dimensions (or mass or strength), or body weight.

Pharmacodynamic parameters dependent on ActRIIB signaling can be measured as endpoints for in vivo testing of ActRIIB binding agents in order to identify those binding agents that are able to neutralize ActRIIB and provide a therapeutic benefit. An ActRIIB neutralizing binding agent is defined as one capable of causing a statistically significant change, as compared to vehicle-treated animals, in such a pharmacodynamic parameter. Such in vivo testing can be performed in any suitable mammal (e.g. mouse, rat, monkey).

3. Screening Assays and Other Biochemical Uses

In certain aspects, the present invention relates to the use of the subject ActRIIB binding agents to identify compounds (agents) which are agonist or antagonists of ActRIIB. Compounds identified through this screening can be tested to assess their ability to modulate ActRIIB-mediated signaling in vivo or in vitro. These compounds can be tested, for example, in animal models.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In a specific embodiment, the test agent is a small organic molecule having a molecular weight of less than about 2,000 Daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ActRIIB binding agent and an ActRIIB polypeptide.

Merely to illustrate, in an exemplary screening assay of the present invention, the compound of interest is contacted with an isolated and purified ActRIIB binding agent which is ordinarily capable of binding to an ActRIIB polypeptide, as appropriate for the intention of the assay. To the mixture of the compound and ActRIIB binding agent is then added a composition containing an ActRIIB polypeptide. Detection and quantification of complexes between ActRIIB polypeptide and ActRIIB binding agent provides a means for determining the compound's efficacy at inhibiting (or potentiating) complex formation between the ActRIIB polypeptide and ActRIIB binding agent. The efficacy of the compound can be assessed by generating dose response curves from data obtained using various concentrations of the test compound. Moreover, a control assay can also be performed to provide a baseline for comparison. For example, in a control assay, isolated and purified ActRIIB binding agent is added to a composition containing an ActRIIB polypeptide, and the formation of complexes between ActRIIB polypeptide and ActRIIB binding agent is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between ActRIIB polypeptide and ActRIIB binding agent may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled ActRIIB polypeptide or ActRIIB binding agent, by immunoassay, or by chromatographic detection.

4. Formulation and Delivery of Therapeutics

Pharmaceutical compositions are provided, comprising one of the above-described binding agents such as antibody Ab-17G05 or a humanized version thereof, along with a pharmaceutically or physiologically acceptable carrier, excipient, or diluent.

The development of suitable dosing and treatment regimens for using the particular compositions described herein in a variety of treatment regimens, including e.g., subcutaneous, oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard-or soft-shell gelatin capsule, or they may be compressed into tablets, or they may be incorporated directly with the food of the diet.

In certain circumstances it will be desirable to deliver the pharmaceutical compositions disclosed herein subcutaneously, parenterally, intravenously, intramuscularly, or even intraperitoneally. Such approaches are well known to the skilled artisan, some of which are further described, for example, in U.S. Pat. Nos. 5,543,158; 5,641,515 and 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. Prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, Remington's Pharmaceutical Sciences, 15th ed., pp. 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologies standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol. 16(7):307-21, 1998; Takakura, Nippon Rinsho 56(3):691-95, 1998; Chandran et al., Indian J. Exp. Biol. 35(8):801-09, 1997; Margalit, Crit. Rev. Ther. Drug Carrier Syst. 12(2-3):233-61, 1995; U.S. Pat. Nos. 5,567,434; 5,552,157; 5,565,213; 5,738,868 and 5,795,587, each specifically incorporated herein by reference in its entirety). The use of liposomes does not appear to be associated with autoimmune responses or unacceptable toxicity after systemic delivery. In certain embodiments, liposomes are formed from phospholipids that are dispersed in an aqueous medium and spontaneously form multilamellar concentric bilayer vesicles (also termed multilamellar vesicles (MLVs)).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev. Ind. Pharm. 24(12): 1113-28, 1998). To avoid side effects due to intracellular polymeric overloading, such ultrafine particles (sized around 0.1 um) may be designed using polymers able to be degraded in vivo. Such particles can be made as described, for example, by Couvreur et al., Crit. Rev. Ther. Drug Carrier Syst. 5(1):1-20, 1988; zur Muhlen et al., Eur. J. Pharm. Biopharm. 45(2):149-55, 1998; Zambaux et al., J Controlled Release 50(1-3):31-40, 1998; and U.S. Pat. No. 5,145,684.

In addition, pharmaceutical compositions of the present invention may be placed within containers, along with packaging material that provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) that may be necessary to reconstitute the pharmaceutical composition.

The dose administered may range from 0.01 mg/kg to 200 mg/kg of body weight, and optionally between 0.5 mg/kg and 20 mg/kg. However, as will be evident to one of skill in the art, the amount and frequency of administration will depend, of course, on such factors as the nature and severity of the indication being treated, the desired response, the condition of the patient, and so forth. Typically, the compositions may be administered by a variety of techniques, as noted above.

5. Therapeutic Uses of ActRIIB Binding Agents

In certain embodiments, ActRIIB binding agents of the present invention can be used for treating or preventing a disease or condition that is associated with abnormal activity of ActRIIB and/or an ActRIIB ligand (e.g., activin A, GDF8, or GDF11). These diseases, disorders or conditions are generally referred to herein as "ActRIIB-associated conditions." In certain embodiments, the present invention provides methods of treating or preventing a disease, disorder, or condition in an individual in need thereof through administering to the individual a therapeutically effective amount of an ActRIIB binding agent as described above. These methods are particularly aimed at therapeutic and prophylactic treatments of animals, and more particularly, humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes prophylaxis of the named condition or amelioration or elimination of the condition once it has been established.

ActRIIB and ActRIIB-ligand complexes play essential roles in tissue growth as well as early developmental processes such as the correct formation of various structures or in one or more post-developmental capacities including sexual development, pituitary hormone production, and creation of bone and cartilage. Thus, ActRIIB-associated conditions include abnormal tissue growth and developmental defects. In addition, ActRIIB-associated conditions include, but are not limited to, disorders of cell growth and differentiation such as inflammation, allergy, autoimmune diseases, infectious diseases, and tumors.

Exemplary ActRIIB-associated conditions include neuromuscular disorders (e.g., muscular dystrophy and muscle atrophy), congestive obstructive pulmonary disease or pulmonary emphysema (and associated muscle wasting), muscle wasting syndrome, sarcopenia, cachexia, adipose tissue disorders (e.g., obesity), type 2 diabetes, and bone degenerative disease (e.g., osteoporosis). Other exemplary ActRIIB-associated conditions include musculodegenerative and neuromuscular disorders, tissue repair (e.g., wound healing), neurodegenerative diseases (e.g., amyotrophic lateral sclerosis), immunologic disorders (e.g., disorders related to abnormal proliferation or function of lymphocytes), and obesity or disorders related to abnormal proliferation of adipocytes.

In certain embodiments, ActRIIB binding agents of the invention are used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines.

Exemplary muscular dystrophies that can be treated with a regimen including the subject ActRIIB binding agents include: Duchenne muscular dystrophy (DMD), Becker muscular dystrophy (BMD), Emery-Dreifuss muscular dystrophy (EDMD), limb-girdle muscular dystrophy (LGMD), fascioscapulohumeral muscular dystrophy (FSH or FSHD) (also known as Landouzy-Dejerine), myotonic muscular dystrophy (MMD) (also known as Steinert's Disease), oculopharyngeal muscular dystrophy (OPMD), distal muscular dystrophy (DD), congenital muscular dystrophy (CMD), and scapulohumeral muscular dystrophy (SMD).

Duchenne muscular dystrophy (DMD) was first described by the French neurologist Guillaume Benjamin Amand Duchenne in the 1860s. Becker muscular dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is broken. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

BMD results from different mutations in the dystrophin gene. BMD patients have some dystrophin, but it is either insufficient in quantity or poor in quality. Having some dystrophin protects the muscles of those with BMD from degenerating as badly or as quickly as those of people with DMD.

For example, studies demonstrate that blocking or eliminating function of GDF8 (an ActRIIB ligand) in vivo can effectively treat at least certain symptoms in DMD and BMD patients. Thus, the subject ActRIIB binding agents may act as GDF8 inhibitors (antagonists), and constitute an alternative means of blocking the functions of GDF8 and/or ActRIIB in vivo in DMD and BMD patients.

In other embodiments, ActRIIB binding agents may also be used to treat or prevent muscular atrophy due to myopathies, examples of which include inflammatory myopathy, metabolic myopathy, and myotonia. Subject ActRIIB binding agents have application in treating congenital myopathies such as myotubular myopathy, nemalene myopathy, and mitochondrial myopathy. The subject ActRIIB binding agents may be used to treat inclusion body myositis, myoglobinurias, rhabdomyolysis, myositis ossificans, polymyositis, or dermatomyositis. In addition, ActRIIB binding agents may treat or prevent muscle atrophy arising from glucocorticoid treatment, sarcopenia, prolonged bed rest, skeletal immobilization, sepsis, or congestive heart failure.

The subject ActRIIB binding agents provide an effective means to increase muscle mass in other neuromuscular diseases or conditions that are in need of muscle growth. For example, amyotrophic lateral sclerosis (ALS, also known as Lou Gehrig's disease or motor neuron disease) is a chronic, incurable, and unstoppable CNS disorder that attacks the motor neurons, components of the CNS that connect the brain to the skeletal muscles. In ALS, the motor neurons deteriorate and eventually die, and though a person's brain normally remains fully functioning and alert, the command to move cannot reach the muscles. Most people who develop ALS are between 40 and 70 years old. The first motor neurons that weaken are those leading to the arms or legs. Those with ALS may have trouble walking, they may drop things, fall, slur their speech, and laugh or cry uncontrollably. Eventually the muscles in the limbs begin to atrophy from disuse. This muscle weakness will become debilitating and a person will need a wheel chair or become unable to function out of bed. Most ALS patients die from respiratory failure or from complications of ventilator assistance like pneumonia, 3-5 years from disease onset. Other neuromuscular diseases in which ActRIIB binding agents may be useful include paralysis due to spinal cord injury or stroke; denervation due to trauma or degenerative, metabolic, or inflammatory neuropathy; adult motor neuron disease; autoimmune motor neuropathy with multifocal conductor block; and infantile or juvenile spinal muscular atrophy.

Increased muscle mass induced by ActRIIB binding agents might also benefit those suffering from muscle wasting diseases. Gonzalez-Cadavid et al. (1998, Proc. Natl. Acad. Sci. USA 95:14938-43) reported that that GDF8 expression correlates inversely with fat-free mass in humans and that increased expression of the GDF8 gene is associated with weight loss in men with AIDS wasting syndrome. By inhibiting the function of GDF8 in AIDS patients, at least certain symptoms of AIDS may be alleviated, if not completely eliminated, thus significantly improving quality of life in AIDS patients.

The cancer anorexia-cachexia syndrome is among the most debilitating and life-threatening aspects of cancer. Progressive weight loss in cancer anorexia-cachexia syndrome is a common feature of many types of cancer and is responsible not only for a poor quality of life and poor response to chemotherapy, but also a shorter survival time than is found in patients with comparable tumors without weight loss. Associated with anorexia, fat and muscle tissue wasting, psychological distress, and a lower quality of life, cachexia arises from a complex interaction between the cancer and the host. It is one of the most common causes of death among cancer patients and is present in 80% at death. It is a complex example of metabolic chaos effecting protein, carbohydrate, and fat metabolism. Tumors produce both direct and indirect abnormalities, resulting in anorexia and weight loss. Currently, there is no treatment to control or reverse the process. Cancer anorexia-cachexia syndrome affects cytokine production, release of lipid-mobilizing and proteolysis-inducing factors, and alterations in intermediary metabolism. Although anorexia is common, a decreased food intake alone is unable to account for the changes in body composition seen in cancer patients, and increasing nutrient intake is unable to reverse the wasting syndrome. Cachexia is generally suspected in patients with cancer if an involuntary weight loss of greater than five percent of premorbid weight occurs within a six-month period.

Since systemic overexpression of GDF8 in adult mice was found to induce profound muscle and fat loss analogous to that seen in human cachexia syndromes (Zimmers et al., 2002, Science 296:1486-1488), the subject ActRIIB binding agents as pharmaceutical compositions can be beneficially used to prevent, treat, or alleviate the symptoms of the cachexia syndrome, where muscle growth is desired. This would include cachexia associated with cancer as well as cachexia associated with rheumatoid arthritis.

In other embodiments, the present invention provides methods of inducing bone and/or cartilage formation, preventing bone loss, increasing bone mineralization or preventing the demineralization of bone. For example, the subject ActRIIB binding agents identified in the present invention have application in treating osteoporosis and the healing of bone fractures and cartilage defects in humans and other animals. ActRIIB binding agents may be useful in patients that are diagnosed with subclinical low bone density, as a protective measure against the development of osteoporosis.

In one specific embodiment, methods and compositions of the present invention may find medical utility in the healing of bone fractures and cartilage defects in humans and other animals. The subject methods and compositions may also have prophylactic use in closed as well as open fracture reduction and also in the improved fixation of artificial joints. De novo bone formation induced by an osteogenic agent contributes to the repair of congenital, trauma-induced, or oncologic resection induced craniofacial defects, and also is useful in cosmetic plastic surgery. Further, methods and compositions of the invention may be used in the treatment of periodontal disease, and in other tooth repair processes. In certain cases, the subject ActRIIB binding agents may provide an environment to attract bone-forming cells, stimulate growth of bone-forming cells or induce differentiation of progenitors of bone-forming cells. ActRIIB binding agents of the invention may also be useful in the treatment of osteoporosis. Further, ActRIIB binding agents may be used in cartilage defect repair and prevention/reversal of osteoarthritis.

In another specific embodiment, the invention provides a therapeutic method and composition for repairing fractures and other conditions related to cartilage and/or bone defects or periodontal diseases. The invention further provides therapeutic methods and compositions for wound healing and tissue repair. The types of wounds include, but are not limited to, burns, incisions and ulcers. See e.g., PCT Publication No. WO84/01106. Such compositions comprise a therapeutically effective amount of at least one of the ActRIIB binding agents of the invention in admixture with a pharmaceutically acceptable vehicle, carrier or matrix.

In another specific embodiment, methods and compositions of the invention can be applied to conditions causing bone loss such as osteoporosis, hyperparathyroidism, Cushing's disease, thyrotoxicosis, chronic diarrheal state or malabsorption, renal tubular acidosis, or anorexia nervosa. Many people know that being female, having a low body weight, and leading a sedentary lifestyle are risk factors for osteoporosis (loss of bone mineral density, leading to fracture risk). However, osteoporosis can also result from the long-term use of certain medications. Osteoporosis resulting from drugs or another medical condition is known as secondary osteoporosis. In a condition known as Cushing's disease, the excess amount of cortisol produced by the body results in osteoporosis and fractures. The most common medications associated with secondary osteoporosis are the corticosteroids, a class of drugs that act like cortisol, a hormone produced naturally by the adrenal glands. Although adequate levels of thyroid hormones (which are produced by the thyroid gland) are needed for the development of the skeleton, excess thyroid hormone can decrease bone mass over time. Antacids that contain aluminum can lead to bone loss when taken in high doses by people with kidney problems, particularly those undergoing dialysis. Other medications that can cause secondary osteoporosis include phenytoin (Dilantin) and barbiturates that are used to prevent seizures; methotrexate (Rheumatrex, Immunex, Folex PFS), a drug for some forms of arthritis, cancer, and immune disorders; cyclosporine (Sandimmune, Neoral), a drug used to treat some autoimmune diseases and to suppress the immune system in organ transplant patients; luteinizing hormone-releasing hormone agonists (Lupron, Zoladex), used to treat prostate cancer and endometriosis; heparin (Calciparine, Liquaemin), an anticlotting medication; and cholestyramine (Questran) and colestipol (Colestid), used to treat high cholesterol. Gum disease causes bone loss because these harmful bacteria in our mouths force our bodies to defend against them. The bacteria produce toxins and enzymes under the gum-line, causing a chronic infection.

In a further embodiment, the present invention provides methods and therapeutic agents for treating diseases or disorders associated with abnormal or unwanted bone growth. For example, patients having the disease known as Fibrodysplasia Ossificans Progressiva (FOP) grow an abnormal "second skeleton" that prevents any movement. Additionally, abnormal bone growth can occur after hip replacement surgery and thus ruin the surgical outcome. This is a more common example of pathological bone growth and a situation in which the subject methods and compositions may be therapeutically useful. The same methods and compositions may also be useful for treating other forms of abnormal bone growth (e.g., pathological growth of bone following trauma, burns or spinal cord injury), and for treating or preventing the undesirable conditions associated with the abnormal bone growth seen in connection with metastatic prostate cancer or osteosarcoma. Examples of these therapeutic agents include, but are not limited to, ActRIIB binding agents that specifically bind to an ActRIIB receptor such that an ActRIIB ligand cannot bind to the ActRIIB receptor.

In other embodiments, the present invention provides compositions and methods for regulating body fat content in an animal and for treating or preventing conditions related thereto, and particularly, health-compromising conditions related thereto. According to the present invention, to regulate (control) body weight can refer to reducing or increasing body weight, reducing or increasing the rate of weight gain, or increasing or reducing the rate of weight loss, and also includes actively maintaining, or not significantly changing body weight (e.g., against external or internal influences which may otherwise increase or decrease body weight). One embodiment of the present invention relates to regulating body weight by administering to an animal (e.g., a human) in need thereof an ActRIIB binding agent.

In one specific embodiment, the present invention relates to methods and ActRIIB binding agents for reducing body weight and/or reducing weight gain in an animal, and more particularly, for treating or ameliorating obesity in patients at risk for or suffering from obesity. Loss of GDF8 (an ActRIIB ligand) function is associated with fat loss without diminution of nutrient intake (McPherron et al., 1997, Proc. Natl. Acad. Sci. USA, 94:12457-12461). In another specific embodiment, the present invention is directed to methods and compounds for treating an animal that is unable to gain or retain weight (e.g., an animal with a wasting syndrome). Such methods are effective to increase body weight and/or mass, or to reduce weight and/or mass loss, or to improve conditions associated with or caused by undesirably low (e.g., unhealthy) body weight and/or mass. The subject ActRIIB binding agents may further be used as a therapeutic agent for slowing or preventing the development of type II diabetes and metabolic syndrome.

EXEMPLIFICATION

The invention now being generally described, it will be more readily understood by reference to the following examples, which are included merely for purposes of illustration of certain embodiments of the present invention, and are not intended to limit the invention.

Example 1

Selection, Prescreening, and Sequencing of ActRIIB-Binding Fabs

A multi-round selection procedure was used to screen for Fabs that displace ligand binding from human ActRIIB with high affinity. Dyax's Fab310 phage-display library (Hoet et al., 2005, Nat Biotechnol 23:344-348) was screened with both a biotinylated human ActRIIB ECD target and a fusion protein target consisting of human ActRIIB ECD linked to biotinylated human IgG1 Fc (ActRIIB-Fc), each target previously immobilized on magnetic streptavidin beads and validated by SDS-polyacrylamide gel electrophoresis. To increase the probability of obtaining ligand-blocking Fabs, an additional selection strategy involved multiple rounds in which the Fab library was 'depleted' by exposure to a complex consisting of biotinylated activin A bound to histidine-tagged ActRIIB ECD. In this way, Fabs which bound to regions outside the ActRIIB ligand-binding site were preferentially removed from the library. Three rounds of such library depletion alternated with three rounds of positive selection using either of the aforementioned targets.

Individual selected clones were tested in a prescreening phage ELISA. In this assay, amplified phage supernatant from each clone was added to ELISA plates onto which biotinylated ActRIIB had been immobilized, and bound M13 phage was detected with a horseradish-peroxidase-conjugated antibody against the P8 major coat protein. Selection outputs yielding positive data from this prescreen ELISA analysis, defined as signal greater than three times background, were carried forward for reformatting to generate soluble sFab-producing clones. Reformatting involves excision of gIII-encoding DNA from isolated phagemid vector to convert Fab cassette DNA to a vector format suitable for sFab expression in *E. coli*. Specifically, polyclonal phagemid DNA was isolated from each selection output; gIII DNA was removed from circular, double-stranded phagemid DNA by restriction digestion with MluI; the linearized DNA was purified and religated; and host *E. coli* was transformed with ligation product to obtain clonal transformants containing vector expressing sFab.

To identify clones expressing sFabs that bind ActRIIB, the reformatted clones were subjected to high-throughput plating, picking, and additional screening by ELISA. This ELISA screening format differed from that described above for the Fab-phage ELISA in that supernatant from sFab cultures was added to the ELISA wells and sFab bound to immobilized ActRIIB was detected by anti-Fab antibody. Those reformatted clones displaying a sFab ELISA signal greater than two times background were rearrayed and subjected to confirmatory ELISA and high-throughput DNA sequencing of the VH and VL regions. Ninety-five sFab clones were initially identified as most promising leads based on the sFab ELISA analysis and sequencing results described above.

Example 2

Characterization and Production of Lead ActRIIB-Binding Fabs

The 95 sFab clones were cultured on a small scale, affinity-purified with protein A, and subjected to additional characterization. At Dyax, purified sFabs were immobilized on a surface plasmon resonance (SPR) microarray chip and exposed to ActRIIB ECD or ActRIIB-Fc fusion protein in a high-throughput assay to determine approximate on-and off-rates. sFabs were ranked by off-rate ($k_d$) rather than equilibrium dissociation constant ($K_D$) due to bivalency of the target protein (confounding avidity effects), and thirteen sFabs were obtained with off-rates less than $10^{-4}$ $s^{-1}$, as well as an additional 50 sFabs with off-rates less than $10^{-3}$ $s^{-1}$. A competition assay was also performed to identify sFabs that compete for the ligand-binding site on ActRIIB. Specifically, immobilized sFabs were exposed to a complex of ActRIIB ECD or ActRIIB-Fc fusion protein with activin A (in a ratio of 1 μM:100 nM) and the signal associated with sFab binding to this complex was compared with that of sFab binding to ActRIIB alone. sFabs whose signal was reduced at least 50% by the presence of activin A were classified as competitors, and 72 of 95 sFabs met this criterion. Potential cross-reactivity with ActRIIA-Fc was also evaluated by SPR and was found to occur for 11 of 95 sFabs.

Affinity-purified sFabs were also screened in two SPR-based competition assays at Acceleron. The first assay evaluated the effect of sFab pretreatment on binding of GDF11 to immobilized ActRIIB-Fc. Specifically, biotinylated ActRIIB-Fc was immobilized on a BIACORE™ streptavidin chip and exposed to GDF11 (500 ng/ml) to determine the SPR signal associated with maximum activin binding (Emax). This signal was compared with a second signal (residual GDF11 binding) resulting from GDF11 binding to immobilized ActRIIB-Fc that had first been exposed to sFab (40 μg/ml). In this assay, a Fab was considered neutralizing if residual GDF11 binding was less than 50% of Emax, and five sFabs (17A07, 17A11, 17C09, 17G01, and 17G05) of the 95 screened met this criterion. A second assay evaluated the effect of sFab pretreatment on ActRIIB binding to immobilized activin A. In this case, biotinylated activin A was immobilized on a BIACORE™ streptavidin chip and exposed to ActRIIB-Fc (1 g/ml) to determine the SPR signal associated with maximum activin A binding (Emax). This signal was compared with residual binding of activin A to a complex of sFab with ActRIIB-Fc, which was formed by premixing these proteins in a 20:1 ratio (20 μg/ml Fab and 1 μg/ml ActRIIB-Fc). sFabs were ranked according to residual binding, and 19 of 95 sFabs screened exhibited residual binding less than 50% of Emax in this assay.

Based on the foregoing analyses, 24 sFab clones with preferred characteristics (such as slow off-rate, inhibition of ligand binding, and low cross-reactivity with ActRIIA) were chosen for scaled-up production. Protein levels of approximately 50 μg were obtained for the majority of clones after one-step purification with protein A. Purified sFab proteins were subjected to confirmatory characterization by ELISA and SDS-polyacrylamide gel electrophoresis before transfer to Acceleron in these larger quantities. DNA sequences of the 24 preferred clones were also confirmed at this stage by standard methods.

Example 3

Sequences of Lead ActRIIB-Binding Fabs

Of the 24 sFabs with preferred characteristics, four were selected for more detailed characterization. Shown below are the amino acid sequences of VH and VL, respectively, for Fab-17A11 (CDR sequences are underlined).

```
                                                     (SEQ ID NO: 3)
  1 EVQLLESGGG LVQPGGSLRL SCAASGFTFS TYAMMWVRQA PGKGLEWVSR

 51 IYPSGGTTTY ADSVKGRFTI SRDNSKNTLY LQMNSLRAED TAVYYCARGS

101 AASSYWGQGT LVTVSS
```

```
                                                     (SEQ ID NO: 4)
  1 QDIQMTQSPS FLSASVGDRV TITCRASQGI SNYLAWYQQK PGKAPKLLIY

 51 AASTLQSGVP SRFSGSGSGT EFTLTISSLQ PEDIGTYYCQ QLISYPFTFG

101 PGTKVDIK
```

Shown below are nucleotide sequences encoding VH and VL, respectively, for Fab-17A11.

```
                                                     (SEQ ID NO: 5)
  1 GAAGTTCAAT TGTTAGAGTC TGGTGGCGGT CTTGTTCAGC CTGGTGGTTC

 51 TTTACGTCTT TCTTGCGCTG CTTCCGGATT CACTTTCTCT ACTTACGCTA

101 TGATGTGGGT TCGCCAAGCT CCTGGTAAAG GTTTGGAGTG GGTTTCTCGT

151 ATCTATCCTT CTGGTGGCAC TACTACTTAT GCTGACTCCG TTAAAGGTCG

201 CTTCACTATC TCTAGAGACA ACTCTAAGAA TACTCTCTAC TTGCAGATGA

251 ACAGCTTAAG GGCTGAGGAC ACGGCCGTGT ATTACTGTGC GAGGGGATCA

301 GCTGCCAGCT CCTACTGGGG CCAGGGAACC CTGGTCACCG TCTCAAGC
```

```
                                                     (SEQ ID NO: 6)
  1 CAAGACATCC AGATGACCCA GTCTCCATCC TTCCTGTCTG CATCTGTTGG

 51 AGACAGGGTC ACCATCACTT GCCGGGCCAG TCAGGGCATT AGCAATTATT

101 TAGCCTGGTA TCAGCAAAAA CCAGGGAAAG CCCCTAAGCT CCTGATCTAT

151 GCTGCATCCA CTTTGCAAAG TGGGGTCCCA TCAAGGTTCA GCGGCAGTGG

201 ATCTGGGACA GAATTCACTC TCACAATCAG CAGCCTGCAG CCTGAAGATA

251 TTGGAACTTA TTACTGTCAA CAGCTTATTA GTTACCCATT CACTTTCGGC

301 CCTGGGACCA AAGTGGATAT CAAA
```

Shown below are the amino acid sequences of VH and VL, respectively, for Fab-17C09 (CDR sequences are underlined).

```
                                                     (SEQ ID NO: 7)
  1 EVQLLESGGG LVQPGGSLRL SCAASGFTFS QYNMTWVRQA PGKGLEWVSS

 51 IYSSGGVTPY ADSVKGRFTI SRDNSKNTLY LQMNSLRAED TAVYYCARGR

101 LLFDYWGQGT LVTVSS
```

-continued (SEQ ID NO: 8)

1 QDIQMTQSPS SLSASVGDRV TITCRASQSI SNYLNWYQQR PGKPPKLLIY

51 AASSLQSGVP SRFSGSGSGT DFSLSISILQ PEDFATYYCQ QGYTAPRSFG

101 QGTKVEIK

Shown below are nucleotide sequences encoding VH and VL, respectively, for Fab-17C09.

(SEQ ID NO: 9)

1 GAAGTTCAAT TGTTAGAGTC TGGTGGCGGT CTTGTTCAGC CTGGTGGTTC

51 TTTACGTCTT TCTTGCGCTG CTTCCGGATT CACTTTCTCT CAGTACAATA

101 TGACTTGGGT TCGCCAAGCT CCTGGTAAAG GTTTGGAGTG GGTTTCTTCT

151 ATCTATTCTT CTGGTGGCGT TACTCCTTAT GCTGACTCCG TTAAAGGTCG

201 CTTCACTATC TCTAGAGACA ACTCTAAGAA TACTCTCTAC TTGCAGATGA

251 ACAGCTTAAG GGCTGAGGAC ACGGCCGTGT ATTACTGTGC GAGAGGTCGC

301 CTCCTCTTTG ACTACTGGGG CCAGGGAACC CTGGTCACCG TCTCAAGC (SEQ ID NO: 10)

1 CAAGACATCC AGATGACCCA GTCTCCATCC TCCCTGTCTG CATCTGTCGG

51 AGACAGAGTC ACCATCACTT GCCGGGCAAG TCAGAGCATT AGCAACTATT

101 TAAATTGGTA TCAGCAGAGA CCAGGGAAAC CCCCTAAGCT CCTGATCTAT

151 GCTGCATCCA GTTTGCAAAG TGGGGTCCCA TCAAGGTTTA GCGGCAGTGG

201 ATCTGGGACA GATTTCAGTC TCTCCATCAG CATTCTGCAA CCTGAAGATT

251 TTGCAACTTA CTACTGTCAA CAGGGTTACA CTGCCCCTCG CAGTTTTGGC

301 CAGGGGACCA AGGTGGAGAT CAAA

Shown below are the amino acid sequences of VH and VL, respectively, for Fab-17G01 (CDR sequences are underlined).

(SEQ ID NO: 11)

1 EVQLLESGGG LVQPGGSLRL SCAASGFTFS NYQMDWVRQA PGKGLEWVSY

51 IGPSGGRTKY ADSVKGRFTI SRDNSKNTLY LQMNSLRAED TATYYCARGL

101 YSFDYWGQGT LVTVSS (SEQ ID NO: 12)

1 QDIQMTQSPS SLSASVGDRV TITCRAGQSI SNFLNWYQHT PGTGPKVLIY

51 AASSLQSGVP SRFSGSGSGT EFTLTITNLQ PEDFATYYCQ QSYSTPFTFG

101 PGTKVDIK

Shown below are nucleotide sequences encoding VH and VL, respectively, for Fab-17G01.

(SEQ ID NO: 13)

1 GAAGTTCAAT TGTTAGAGTC TGGTGGCGGT CTTGTTCAGC CTGGTGGTTC

51 TTTACGTCTT TCTTGCGCTG CTTCCGGATT CACTTTCTCT AATTACCAGA

101 TGGATTGGGT TCGCCAAGCT CCTGGTAAAG GTTTGGAGTG GGTTTCTTAT

151 ATCGGTCCTT CTGGTGGCCG TACTAAGTAT GCTGACTCCG TTAAAGGTCG

201 CTTCACTATC TCTAGAGACA ACTCTAAGAA TACTCTCTAC TTGCAGATGA

-continued

```
251  ACAGCTTAAG GGCTGAGGAC ACAGCCACAT ATTACTGTGC GAGAGGATTG

301  TACTCGTTTG ACTACTGGGG CCAGGGAACC CTGGTCACCG TCTCAAGC
```

(SEQ ID NO: 14)

```
  1  CAAGACATCC AGATGACCCA GTCTCCATCC TCCCTGTCTG CATCTGTAGG

 51  AGACAGAGTC ACCATCACTT GCCGGGCAGG TCAGAGCATT AGCAACTTTT

101  TAAATTGGTA TCAGCATACA CCAGGGACAG GCCCTAAAGT CCTGATCTAT

151  GCTGCATCCA GTTTGCAAAG TGGGGTCCCA TCACGGTTCA GTGGCAGTGG

201  ATCTGGGACA GAATTCACTC TCACCATCAC CAATCTGCAA CCTGAAGATT

251  TTGCAACTTA CTACTGTCAA CAGAGTTACA GTACCCCATT CACTTTCGGC

301  CCTGGGACCA AAGTGGATAT CAAG
```

Shown below are the amino acid sequences of VH and VL, respectively, for Fab-17G05 (CDR sequences are underlined).

(SEQ ID NO: 15)

```
  1  EVQLLESGGG LVQPGGSLRL SCAASGFTFS NYWMGWVRQA PGKGLEWVSY

 51  IRSSGGLTHY ADSVKGRFTI SRDNSKNTLY LQMNSLRAED TATYYCAKGL

101  YSFDYWGQGT LVTVSS
```

(SEQ ID NO: 16)

```
  1  QDIQMTQSPS SLSASVGDRV TITCRASQGV NNFLAWYQQK PGKAPRLLIY

 51  AASTLQSGVP SRFSGSGSGT DFTLSISNLQ PEDFATYYCQ QSYSTPRGFG

101  QGTKVEIK
```

Shown below are nucleotide sequences encoding VH and VL, respectively, for Fab-17G05.

(SEQ ID NO: 17)

```
  1  GAAGTTCAAT TGTTAGAGTC TGGTGGCGGT CTTGTTCAGC CTGGTGGTTC

 51  TTTACGTCTT TCTTGCGCTG CTTCCGGATT CACTTTCTCT AATTACTGGA

101  TGGGTTGGGT TCGCCAAGCT CCTGGTAAAG GTTTGGAGTG GGTTTCTTAT

151  ATCCGTTCTT CTGGTGGCCT TACTCATTAT GCTGACTCCG TTAAAGGTCG

201  CTTCACTATC TCTAGAGACA ACTCTAAGAA TACTCTCTAC TTGCAGATGA

251  ACAGCTTAAG GGCTGAGGAC ACAGCCACAT ATTACTGTGC GAAAGGACTA

301  TATTCCTTTG ACTACTGGGG CCAGGGAACC CTGGTCACCG TCTCAAGC
```

(SEQ ID NO: 18)

```
  1  CAAGACATCC AGATGACCCA GTCTCCATCT TCCCTGTCTG CTTCTGTAGG

 51  AGACAGAGTC ACCATCACTT GCCGGGCCAG TCAGGGCGTT AACAATTTTT

101  TAGCCTGGTA TCAGCAAAAA CCAGGGAAGG CCCCTAGGCT CCTGATCTAT

151  GCTGCATCCA CTTTGCAGAG TGGGGTCCCA TCAAGGTTCA GCGGCAGTGG

201  ATCTGGGACA GATTTCACTC TCTCCATCAG CAACCTGCAG CCTGAAGACT

251  TTGCAACTTA TTACTGTCAA CAGAGTTACA GTACCCCTCG GGGGTTCGGC

301  CAAGGGACCA AGGTGGAAAT CAAA
```

Listed below are CDR sequences for Fab-17A11.

```
CDR-H1    TYAMM              (SEQ ID NO: 19)
CDR-H2    RIYPSGGTTTYADSVKG  (SEQ ID NO: 20)
CDR-H3    GSAASSY            (SEQ ID NO: 21)
CDR-L1    RASQGISNYLA        (SEQ ID NO: 22)
CDR-L2    AASTLQS            (SEQ ID NO: 23)
CDR-L3    QQLISYPFT          (SEQ ID NO: 24)
```

Listed below are CDR sequences for Fab-17C09.

```
CDR-H1    QYNMT              (SEQ ID NO: 25)
CDR-H2    SIYSSGGVTPYADSVKG  (SEQ ID NO: 26)
CDR-H3    GRLLFDY            (SEQ ID NO: 27)
CDR-L1    RASQSISNYLN        (SEQ ID NO: 28)
CDR-L2    AASSLQS            (SEQ ID NO: 29)
CDR-L3    QQGYTAPRS          (SEQ ID NO: 30)
```

Listed below are CDR sequences for Fab-17G01.

```
CDR-H1    NYQMD              (SEQ ID NO: 31)
CDR-H2    YIGPSGGRTKYADSVKG  (SEQ ID NO: 32)
CDR-H3    GLYSFDY            (SEQ ID NO: 33)
CDR-L1    RAGQSISNFLN        (SEQ ID NO: 34)
CDR-L2    AASSLQS            (SEQ ID NO: 35)
CDR-L3    QQSYSTPFT          (SEQ ID NO: 36)
```

Listed below are CDR sequences for Fab-17G05.

```
CDR-H1    NYWMG              (SEQ ID NO: 37)
CDR-H2    YIRSSGGLTHYADSVKG  (SEQ ID NO: 38)
CDR-H3    GLYSFDY            (SEQ ID NO: 39)
CDR-L1    RASQGVNNFLA        (SEQ ID NO: 40)
CDR-L2    AASTLQS            (SEQ ID NO: 41)
CDR-L3    QQSYSTPRG          (SEQ ID NO: 42)
```

Example 4

Characterization of Lead Fab Binding to ActRIIB

Applicants used SPR (BIACORE™-based analysis) to more fully characterize binding of lead sFabs to ActRIIB. FIG. 1 shows kinetic characterization of Fab-17G05 binding to human ActRIIB-hFc (dimeric protein), and the binding parameters for several lead sFabs are indicated below.

| | 25° C. | | | 37° C. | | |
|---|---|---|---|---|---|---|
| Fab | $k_a$ ($M^{-1}s^{-1}$) | $k_d$ ($s^{-1}$) | $K_D$ (M) | $k_a$ ($M^{-1}s^{-1}$) | $k_d$ ($s^{-1}$) | $K_D$ (M) |
| 17G05 | $16 \times 10^5$ | $8.7 \times 10^{-4}$ | $5.5 \times 10^{-10}$ | $26 \times 10^5$ | $3.1 \times 10^{-3}$ | $1.9 \times 10^{-9}$ |
| 575A-M31-E07 | $8.7 \times 10^5$ | $1.6 \times 10^{-4}$ | $18 \times 10^{-10}$ | $11 \times 10^5$ | $5.3 \times 10^{-3}$ | $5 \times 10^{-9}$ |
| 17G01 | $4.6 \times 10^5$ | $18 \times 10^{-4}$ | $38 \times 10^{-10}$ | $5.8 \times 10^5$ | $12 \times 10^{-3}$ | $21 \times 10^{-9}$ |
| 17A11 | $12 \times 10^5$ | $1.9 \times 10^{-4}$ | $16 \times 10^{-10}$ | $14 \times 10^5$ | $14 \times 10^{-3}$ | $9.9 \times 10^{-9}$ |

Among the lead sFabs analyzed, Fab-17G05 displayed the best kinetic parameters for off-rate and $K_D$ at 37° C., and for $K_D$ at 25° C.

Example 5

Reporter Gene Assay in A204 Cells

A reporter gene assay in A204 cells was used to determine the ability of anti-ActRIIB Fabs and recombinant antibodies to neutralize ActRIIB. This assay is based on a human rhabdomyosarcoma cell line transfected with a pGL3 (CAGA)12 reporter plasmid (Dennler et al, 1998, EMBO 17: 3091-3100) as well as a Renilla reporter plasmid (pRL-CMV) to control for transfection efficiency. The CAGA12 motif is present in TGF-beta responsive genes (PAI-1 gene), so this vector is of general use for factors signaling through Smad2 and Smad3. Since the A204 cell line expresses primarily ActRIIA rather than ActRIIB, it is not possible to directly test antibodies for potential ActRIIB neutralizing ability. Instead, this assay was designed to detect the ability of test articles to neutralize the inhibitory effect of the soluble fusion protein ActRIIB-Fc on activation of endogenous ActRIIA by ligands (such as activin A, GDF11 or myostatin) that can bind with high affinity to both ActRIIA and ActRIIB. Thus, in this assay, ligand-mediated activation of ActRIIA will occur despite the presence of ActRIIB-Fc if the anti-ActRIIB Fab or antibody is neutralizing.

On the first day of the assay, A204 cells (ATCC HTB-82) were distributed in 48-well plates at $10^5$ cells per well. On the second day, a solution containing 10 μg pGL3(CAGA) 12, 1 g pRLCMV, 30 μl Fugene 6 (Roche Diagnostics), and 970 μl OptiMEM (Invitrogen) was preincubated for 30 min, then added to McCoy's growth medium, which was applied to the plated cells (500 μl/well) for incubation overnight at room temperature. On the third day, medium was removed, and cells were incubated for 6 h at 37° C. with a mixture of ligands and inhibitors prepared as described below.

To evaluate the neutralizing potency of Fabs or recombinant antibodies, a serial dilution of the test article was made in a 48-well plate in a 200 μl volume of assay buffer (McCoy's medium+0.1% BSA). An equal volume of ActRIIB-Fc (200 μg/ml) in assay buffer was then added. The test solutions were incubated at 37° C. for 30 minutes, then 400 μl of GDF11 (10 ng/ml) or activin A (10 ng/ml) was added to all wells, and 350 μl of this mixture was added to each well of the 48-well plate of A204 cells. Each concentration of Fab or antibody was tested in duplicate. The final concentration of ActRIIB-Fc was 50 ng/ml (which is the IC50 for this inhibitor of activin A signaling when the final concentration of activin A is 5 ng/ml). After incubation with test solutions for 6 h, cells were rinsed with phosphate-buffered saline containing 0.1% BSA, then lysed with passive lysis buffer (Promega E1941) and stored overnight at −70° C. On the fourth and final day, plates were warmed to room temperature with gentle shaking. Cell lysates were transferred in duplicate to a chemoluminescence plate (96-well) and analyzed in a luminometer with reagents from a Dual-Luciferase Reporter Assay system (Promega E1980) to determine normalized luciferase activity.

This reporter gene assay was used to screen several of the lead sFabs. In two different assays with GDF11 as ligand, Fab-17G05 was a more potent neutralizer of cellular signaling than were other sFabs tested, including Fab-17A11 and Fab-17G01.

Example 6

Generation of Ab-17G05 by Fab Conversion

On the basis of the foregoing results, Fab-17G05 was selected for conversion to an antibody. Construction of vectors for expression of human IgG heavy and light chains was based on Persic et al. (1997, Gene 187:9-18). Both vectors use an IgG secretory leader containing a unique restriction site (BssHII) to clone VH and VL at their 5' end. Heavy-chain vector incorporates an adjacent VH linker containing a BstEII site, which is conserved across all VH subgroups, for cloning VH at the 3' end. Thus, VH from Fab-17G05 was generated by PCR and inserted into digested pAID4 human IgG1 heavy-chain vector (BssHII 5' and BstEII 3'). To accommodate the full range of VL subgroups at their 3' boundary, light-chain vector incorporates a VL linker containing a XhoI site, which is available in some VL subgroups, followed by a short intron containing a PacI site, which can be used for cloning all other VL subgroups. Thus, VL from Fab-17G05 was generated by PCR and inserted into digested pAID4 human kappa light-chain vector (BssHII 5' and PacI 3'). The completed constructs underwent confirmatory sequencing and were transiently cotransfected into COS cells. COS conditioned medium was analyzed by Western blot to confirm antibody size and by ELISA for human Fc domain to determine antibody concentration. Antibody was also produced in stably transfected CHO cells. Purification of antibody protein from COS or CHO cell conditioned medium was achieved by protein A chromatography (e.g. MabSelect SuRe™, General Electric, Piscataway, N.J.), dialysis, viral filtration, and buffer exchange. The N-terminus of purified VH protein was confirmed by N-terminal sequencing to be EVQLLESGGG (SEQ ID NO: 43).

Example 7

Characterization of Ab-17G05 Binding to ActRIIB

Figure 2:
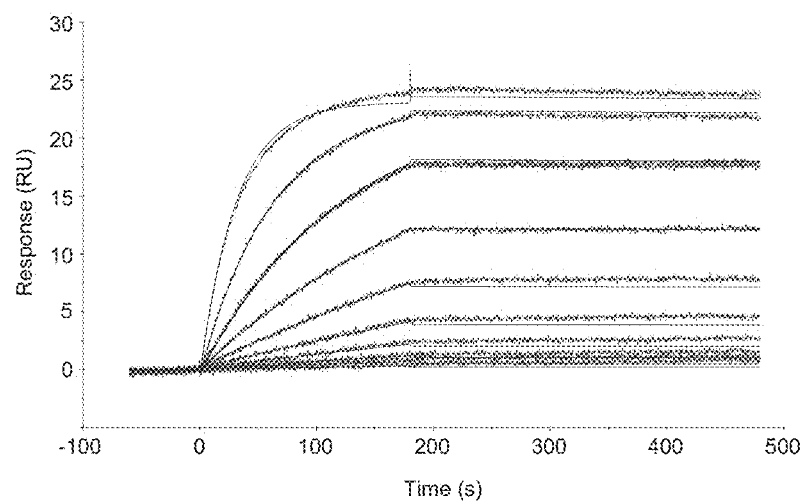
FIG. 2 depicts kinetic characterization of Ab-17G05 binding to hActRIIB-mFc as determined by BIACORE™-based analysis at 25° C. (A) or 37° C. (B). hActRIIB-mFc was captured on a chip with covalently immobilized antibody against murine IgG2a Fc and then exposed to Ab-17G05 at concentrations ranging from 0.0195 μg/ml to 5 μg/ml. The $K_D$ was $2.8\times10^{-11}$ at 25° C. and $9.2\times10^{-11}$ at 37° C.
Figure 2:
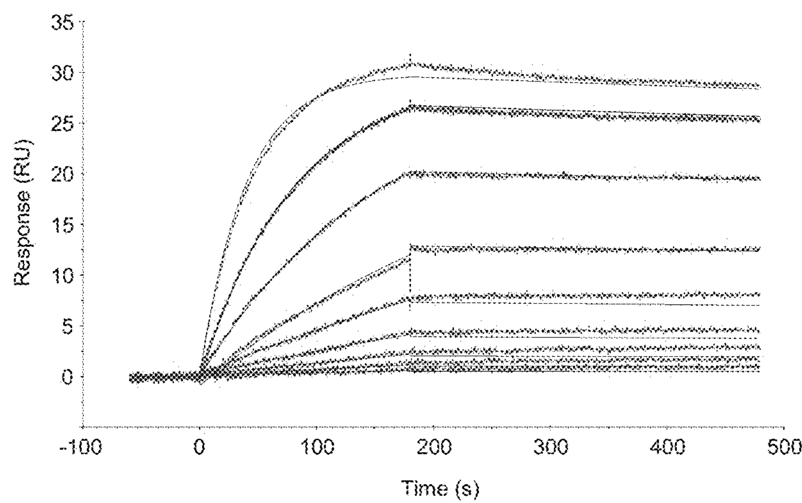

BIACORE™-based analysis was used to characterize binding of Ab-17G05 to ActRIIB. For this analysis, Ab-17G05 was purified from COS-cell-conditioned media by one-step protein G chromatography. FIG. 2 shows kinetic characterization of Ab-17G05 binding to hActRIIB-mFc (dimeric protein), and binding parameters are listed below compared with those of Fab-17G05.

| | 25° C. | | | 37° C. | | |
|---|---|---|---|---|---|---|
| | $k_a$ ($M^{-1}s^{-1}$) | $k_d$ ($s^{-1}$) | $K_D$ (M) | $k_a$ ($M^{-1}s^{-1}$) | $k_d$ ($s^{-1}$) | $K_D$ (M) |
| Ab-17G05 | $9.7 \times 10^5$ | $2.7 \times 10^{-5}$ | $2.8 \times 10^{-11}$ | $1.5 \times 10^6$ | $1.4 \times 10^{-4}$ | $9.2 \times 10^{-11}$ |
| Fab-17G05 | $16 \times 10^5$ | $87 \times 10^{-5}$ | $55 \times 10^{-11}$ | $2.6 \times 10^6$ | $31 \times 10^{-4}$ | $190 \times 10^{-11}$ |

Conversion of Fab-17G05 to an antibody resulted in improvements of 20-fold or greater in off-rate and $K_D$ at both 25° C. or 37° C.

Example 8

Neutralization by Ab-17G05 in a Cell-Based Assay

Figure 3:
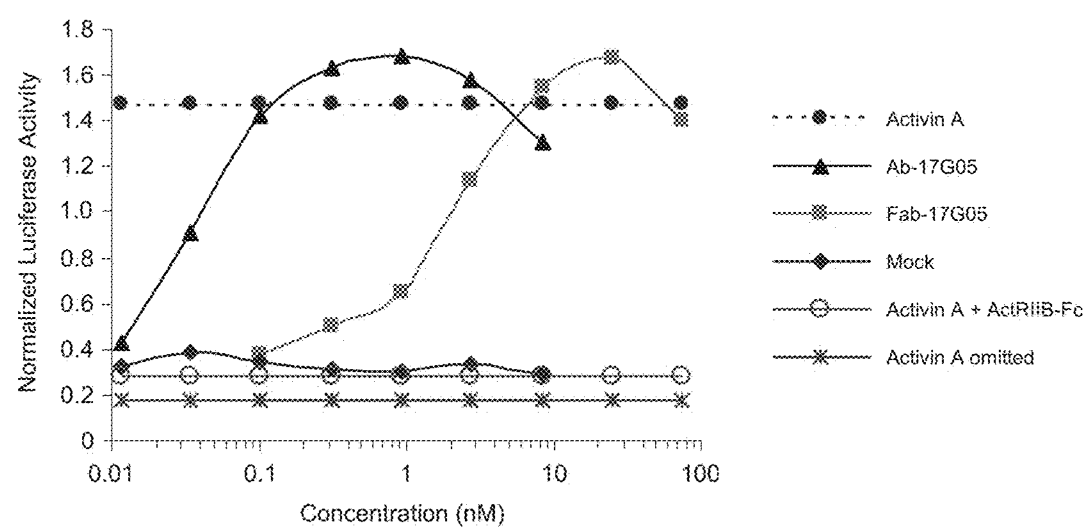
FIG. 3 depicts neutralizing activity of Ab-17G05 or Fab-17G05 in a cell-based reporter gene assay. Included are assay responses with activin A alone (5 ng/ml) and combined activin A and ActRIIB-Fc (50 ng/ml). The potency of Ab-17G05 ($IC_{50}\approx0.04$ nM) in neutralizing the interaction between activin A and ActRIIB-Fc was approximately two orders of magnitude higher than that of Fab-17G05 ($IC_{50}\approx2.6$ nM).

Ab-17G05 was evaluated for its ability to neutralize binding of activin A and ActRIIB in the cell-based reporter gene assay described in Example 4. In this assay, ligand-mediated activation of endogenous ActRIIA will occur despite the presence of exogenous ActRIIB-Fc if the anti-ActRIIB antibody or Fab is neutralizing. Results obtained for Ab-R17G05 are based on conditioned media from COS cells (quantitated by ELISA) and for Fab-R17G05 on material purified with protein A. As shown in FIG. 3, Ab-17G05 was a potent stimulator of activin A signaling through ActRIIA, thus indicating that Ab-17G05 can neutralize ActRIIB binding to activin A in a cell-based system. Unconverted Fab-17G05 also displayed neutralizing capability; however, the potency of Ab-17G05 (IC50≈0.04 nM) was two orders of magnitude higher than that of Fab-17G05 (IC50≈2.6 nM).

Taken together, the foregoing findings demonstrate the generation of an antibody (17G05) capable of binding to ActRIIB with high affinity and potently neutralizing ActRIIB-mediated signaling. Consistent with these findings, Ab-17G05 increases muscle mass in vivo.

Example 9

Detection of Human Anti-ActRIIB Antibodies in Serum

In the course of clinical development of an ActRIIB-Fc fusion protein (known as ACE-031), an ELISA method has been developed to detect neutralizing antibodies to the ActRIIB portion of ActRIIB-Fc in human serum. Briefly, ACE-031 is coated on the microplate followed by control antibody (murine or human anti-ActRIIB; 17G05) and sample incubation. After washing, samples are incubated with biotinylated Activin A and bound ligand is detected with streptavidin horseradish peroxidase (HRP) and tetramethylbenzidine (TMB) substrate. Biotinylated-Activin A binding to ACE-031 in the absence of neutralizing antibody is recorded as max signal, the difference between the max signal and signal obtained in the presence of bound neutralizing antibody (inhibition) is proportional to the amount of neutralization activity against ACE-031 in the sample. Serum samples from human patients treated with ActRIIB-Fc and suspected of having an immune reaction to the ActRIIB-Fc may be evaluated by the same protocol, replacing the control antibody with the serum sample and comparing the measured signal against the standard values generated with the control antibody.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. An isolated polynucleotide sequence encoding an anti-ActRIIB antibody or functional fragment thereof that binds to ActRIIB between amino acids 20-134 of SEQ ID NO: 1, wherein said antibody or functional fragment thereof comprises a variable heavy chain encoded by the nucleic acid sequence of SEQ ID NO: 17 and a variable light chain encoded by the nucleic acid sequence of SEQ ID NO: 18.

2. A cloning or expression vector comprising the isolated polynucleotide sequence according to claim 1.

3. An isolated host cell comprising the vector according to claim 2.

4. A process for the production of an antibody or functional fragment thereof that binds to ActRIIB between amino acids 20-134 of SEQ ID NO: 1, comprising culturing the host cell of claim 3 and isolating the antibody or functional fragment thereof.

* * * * *

SEQUENCE LISTING

```
<160> NUMBER OF SEQ ID NOS: 43

<210> SEQ ID NO 1
<211> LENGTH: 512
<212> TYPE: PRT
<213> ORGANISM: Homo sapiens

<400> SEQUENCE: 1

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335
```

Leu Ala Asp Phe Gly Leu Ala Val Arg Phe Glu Pro Gly Lys Pro Pro
340 345 350

Gly Asp Thr His Gly Gln Val Gly Thr Arg Arg Tyr Met Ala Pro Glu
355 360 365

Val Leu Glu Gly Ala Ile Asn Phe Gln Arg Asp Ala Phe Leu Arg Ile
370 375 380

Asp Met Tyr Ala Met Gly Leu Val Leu Trp Glu Leu Val Ser Arg Cys
385 390 395 400

Lys Ala Ala Asp Gly Pro Val Asp Glu Tyr Met Leu Pro Phe Glu Glu
405 410 415

Glu Ile Gly Gln His Pro Ser Leu Glu Glu Leu Gln Glu Val Val Val
420 425 430

His Lys Lys Met Arg Pro Thr Ile Lys Asp His Trp Leu Lys His Pro
435 440 445

Gly Leu Ala Gln Leu Cys Val Thr Ile Glu Glu Cys Trp Asp His Asp
450 455 460

Ala Glu Ala Arg Leu Ser Ala Gly Cys Val Glu Glu Arg Val Ser Leu
465 470 475 480

Ile Arg Arg Ser Val Asn Gly Thr Thr Ser Asp Cys Leu Val Ser Leu
485 490 495

Val Thr Ser Val Thr Asn Val Asp Leu Pro Pro Lys Glu Ser Ser Ile
500 505 510

<210> SEQ ID NO 2
<211> LENGTH: 1536
<212> TYPE: DNA
<213> ORGANISM: Homo sapiens

<400> SEQUENCE: 2
atgacggcgc cctgggtggc cctcgccctc ctctggggat cgctgtgcgc cggctctggg 60
cgtggggagg ctgagacacg ggagtgcatc tactacaacg ccaactggga gctggagcgc 120
accaaccaga gcggcctgga gcgctgcgaa ggcgagcagg acaagcggct gcactgctac 180
gcctcctggc gcaacagctc tggcaccatc gagctcgtga agaagggctg ctggctagat 240
gacttcaact gctacgatag gcaggagtgt gtggccactg aggagaaccc ccaggtgtac 300
ttctgctgct gtgaaggcaa cttctgcaac gaacgcttca ctcatttgcc agaggctggg 360
ggcccggaag tcacgtacga gccacccccg acagccccca ccctgctcac ggtgctggcc 420
tactcactgc tgcccatcgg gggcctttcc ctcatcgtcc tgctggcctt ttggatgtac 480
cggcatcgca agccccccta cggtcatgtg gacatccatg aggaccctgg gcctccacca 540
ccatcccctc tggtgggcct gaagccactg cagctgctgg agatcaaggc tcgggggcgc 600
tttggctgtg tctggaaggc ccagctcatg aatgactttg tagctgtcaa gatcttccca 660
ctccaggaca agcagtcgtg gcagagtgaa cgggagatct tcagcacacc tggcatgaag 720
cacgagaacc tgctacagtt cattgctgcc gagaagcgag gctccaacct cgaagtagag 780
ctgtggctca tcacggcctt ccatgacaag ggctccctca cggattacct caaggggaac 840
atcatcacat ggaacgaact gtgtcatgta gcagagacga tgtcacgagg cctctcatac 900
ctgcatgagg atgtgccctg gtgccgtggc gagggccaca agccgtctat tgcccacagg 960
gactttaaaa gtaagaatgt attgctgaag agcgacctca cagccgtgct ggctgacttt 1020
ggcttggctg ttcgatttga gccagggaaa cctccagggg acacccacgg acaggtaggc 1080
acgagacggt acatggctcc tgaggtgctc gagggagcca tcaacttcca gagagatgcc 1140

```
ttcctgcgca ttgacatgta tgccatgggg ttggtgctgt gggagcttgt gtctcgctgc   1200

aaggctgcag acggacccgt ggatgagtac atgctgccct ttgaggaaga gattggccag   1260

caccccttcgt tggaggagct gcaggaggtg gtggtgcaca agaagatgag gcccaccatt   1320

aaagatcact ggttgaaaca cccgggcctg gcccagcttt gtgtgaccat cgaggagtgc   1380

tgggaccatg atgcagaggc tcgcttgtcc gcgggctgtg tggaggagcg ggtgtccctg   1440

attcggaggt cggtcaacgg cactacctcg gactgtctcg tttccctggt gacctctgtc   1500

accaatgtgg acctgccccc taaagagtca agcatc                             1536
```

```
<210> SEQ ID NO 3
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Met Trp Val Arg Gln Ala Pro Gly Lys Gly Leu Glu Trp Val
        35                  40                  45

Ser Arg Ile Tyr Pro Ser Gly Gly Thr Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Ala Ala Ser Ser Tyr Trp Gly Gln Gly Thr Leu Val
            100                 105                 110

Thr Val Ser Ser
        115


<210> SEQ ID NO 4
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Asp Ile Gln Met Thr Gln Ser Pro Ser Phe Leu Ser Ala Ser Val
1               5                   10                  15

Gly Asp Arg Val Thr Ile Thr Cys Arg Ala Ser Gln Gly Ile Ser Asn
            20                  25                  30

Tyr Leu Ala Trp Tyr Gln Gln Lys Pro Gly Lys Ala Pro Lys Leu Leu
        35                  40                  45

Ile Tyr Ala Ala Ser Thr Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Ile Gly Thr Tyr Tyr Cys Gln Gln Leu Ile Ser Tyr Pro
                85                  90                  95
```

```
Phe Thr Phe Gly Pro Gly Thr Lys Val Asp Ile Lys
            100                 105


<210> SEQ ID NO 5
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

gaagttcaat tgttagagtc tggtggcggt cttgttcagc ctggtggttc tttacgtctt      60

tcttgcgctg cttccggatt cactttctct acttacgcta tgatgtgggt tcgccaagct     120

cctggtaaag gtttggagtg ggtttctcgt atctatcctt ctggtggcac tactacttat     180

gctgactccg ttaaaggtcg cttcactatc tctagagaca actctaagaa tactctctac     240

ttgcagatga acagcttaag ggctgaggac acggccgtgt attactgtgc gaggggatca     300

gctgccagct cctactgggg ccagggaacc ctggtcaccg tctcaagc                  348


<210> SEQ ID NO 6
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

caagacatcc agatgaccca gtctccatcc ttcctgtctg catctgttgg agacagggtc      60

accatcactt gccgggccag tcagggcatt agcaattatt tagcctggta tcagcaaaaa     120

ccagggaaag cccctaagct cctgatctat gctgcatcca ctttgcaaag tggggtccca     180

tcaaggttca gcggcagtgg atctgggaca gaattcactc tcacaatcag cagcctgcag     240

cctgaagata ttggaactta ttactgtcaa cagcttatta gttacccatt cactttcggc     300

cctgggacca aagtggatat caaa                                            324


<210> SEQ ID NO 7
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Asn Met Thr Trp Val Arg Gln Ala Pro Gly Lys Gly Leu Glu Trp Val
        35                  40                  45

Ser Ser Ile Tyr Ser Ser Gly Gly Val Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Leu Leu Phe Asp Tyr Trp Gly Gln Gly Thr Leu Val
```

```
            100                 105                 110

Thr Val Ser Ser
        115


<210> SEQ ID NO 8
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Asn
            20                  25                  30

Tyr Leu Asn Trp Tyr Gln Gln Arg Pro Gly Lys Pro Pro Lys Leu Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Ser Leu Ser Ile Ser Ile Leu Gln
65                  70                  75                  80

Pro Glu Asp Phe Ala Thr Tyr Tyr Cys Gln Gln Gly Tyr Thr Ala Pro
                85                  90                  95

Arg Ser Phe Gly Gln Gly Thr Lys Val Glu Ile Lys
            100                 105


<210> SEQ ID NO 9
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

gaagttcaat tgttagagtc tggtggcggt cttgttcagc ctggtggttc tttacgtctt      60

tcttgcgctg cttccggatt cactttctct cagtacaata tgacttgggt tcgccaagct     120

cctggtaaag gtttggagtg ggtttcttct atctattctt ctggtggcgt tactccttat     180

gctgactccg ttaaaggtcg cttcactatc tctagagaca actctaagaa tactctctac     240

ttgcagatga acagcttaag ggctgaggac acggccgtgt attactgtgc gagaggtcgc     300

ctcctctttg actactgggg ccagggaacc ctggtcaccg tctcaagc                  348


<210> SEQ ID NO 10
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

caagacatcc agatgaccca gtctccatcc tccctgtctg catctgtcgg agacagagtc      60

accatcactt gccgggcaag tcagagcatt agcaactatt taaattggta tcagcagaga     120

ccagggaaac cccctaagct cctgatctat gctgcatcca gtttgcaaag tggggtccca     180

tcaaggttta gcggcagtgg atctgggaca gatttcagtc tctccatcag cattctgcaa     240
```

-continued

```
cctgaagatt ttgcaactta ctactgtcaa cagggttaca ctgcccctcg cagttttggc    300

caggggacca aggtggagat caaa                                            324


<210> SEQ ID NO 11
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gln Met Asp Trp Val Arg Gln Ala Pro Gly Lys Gly Leu Glu Trp Val
        35                  40                  45

Ser Tyr Ile Gly Pro Ser Gly Gly Arg Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Gly Leu Tyr Ser Phe Asp Tyr Trp Gly Gln Gly Thr Leu Val
            100                 105                 110

Thr Val Ser Ser
        115


<210> SEQ ID NO 12
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Asp Ile Gln Met Thr Gln Ser Pro Ser Ser Leu Ser Ala Ser Val
1               5                   10                  15

Gly Asp Arg Val Thr Ile Thr Cys Arg Ala Gly Gln Ser Ile Ser Asn
            20                  25                  30

Phe Leu Asn Trp Tyr Gln His Thr Pro Gly Thr Gly Pro Lys Val Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Glu Phe Thr Leu Thr Ile Thr Asn Leu Gln
65                  70                  75                  80

Pro Glu Asp Phe Ala Thr Tyr Tyr Cys Gln Gln Ser Tyr Ser Thr Pro
                85                  90                  95

Phe Thr Phe Gly Pro Gly Thr Lys Val Asp Ile Lys
            100                 105


<210> SEQ ID NO 13
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 13

```
gaagttcaat tgttagagtc tggtggcggt cttgttcagc ctggtggttc tttacgtctt     60

tcttgcgctg cttccggatt cactttctct aattaccaga tggattgggt tcgccaagct    120

cctggtaaag gtttggagtg ggtttcttat atcggtcctt ctggtggccg tactaagtat    180

gctgactccg ttaaaggtcg cttcactatc tctagagaca actctaagaa tactctctac    240

ttgcagatga acagcttaag ggctgaggac acagccacat attactgtgc gagaggattg    300

tactcgtttg actactgggg ccagggaacc ctggtcaccg tctcaagc                 348
```

<210> SEQ ID NO 14
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
caagacatcc agatgaccca gtctccatcc tccctgtctg catctgtagg agacagagtc     60

accatcactt gccgggcagg tcagagcatt agcaacttt taaattggta tcagcataca    120

ccagggacag gccctaaagt cctgatctat gctgcatcca gtttgcaaag tggggtccca    180

tcacggttca gtggcagtgg atctgggaca gaattcactc tcaccatcac caatctgcaa    240

cctgaagatt ttgcaactta ctactgtcaa cagagttaca gtaccccatt cactttcggc    300

cctgggacca aagtggatat caag                                           324
```

<210> SEQ ID NO 15
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Gly Trp Val Arg Gln Ala Pro Gly Lys Gly Leu Glu Trp Val
        35                  40                  45

Ser Tyr Ile Arg Ser Ser Gly Gly Leu Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Lys Gly Leu Tyr Ser Phe Asp Tyr Trp Gly Gln Gly Thr Leu Val
            100                 105                 110

Thr Val Ser Ser
        115
```

<210> SEQ ID NO 16
<211> LENGTH: 108
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 16

```
Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Val Asn Asn
            20                  25                  30

Phe Leu Ala Trp Tyr Gln Gln Lys Pro Gly Lys Ala Pro Arg Leu Leu
        35                  40                  45

Ile Tyr Ala Ala Ser Thr Leu Gln Ser Gly Val Pro Ser Arg Phe Ser
    50                  55                  60

Gly Ser Gly Ser Gly Thr Asp Phe Thr Leu Ser Ile Ser Asn Leu Gln
65                  70                  75                  80

Pro Glu Asp Phe Ala Thr Tyr Tyr Cys Gln Gln Ser Tyr Ser Thr Pro
                85                  90                  95

Arg Gly Phe Gly Gln Gly Thr Lys Val Glu Ile Lys
            100                 105
```

<210> SEQ ID NO 17
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
gaagttcaat tgttagagtc tggtggcggt cttgttcagc ctggtggttc tttacgtctt     60

tcttgcgctg cttccggatt cactttctct aattactgga tgggttgggt tcgccaagct    120

cctggtaaag gtttggagtg ggtttcttat atccgttctt ctggtggcct tactcattat    180

gctgactccg ttaaaggtcg cttcactatc tctagagaca actctaagaa tactctctac    240

ttgcagatga acagcttaag ggctgaggac acagccacat attactgtgc gaaaggacta    300

tattcctttg actactgggg ccagggaacc ctggtcaccg tctcaagc                348
```

<210> SEQ ID NO 18
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
caagacatcc agatgaccca gtctccatct tccctgtctg cttctgtagg agacagagtc     60

accatcactt gccgggccag tcagggcgtt aacaattttt tagcctggta tcagcaaaaa    120

ccagggaagg cccctaggct cctgatctat gctgcatcca ctttgcagag tggggtccca    180

tcaaggttca gcggcagtgg atctgggaca gatttcactc tctccatcag caacctgcag    240

cctgaagact ttgcaactta ttactgtcaa cagagttaca gtacccctcg gggttcggc    300

caagggacca aggtggaaat caaa                                          324
```

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic

```
      peptide

<400> SEQUENCE: 19

Thr Tyr Ala Met Met
1               5


<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Ile Tyr Pro Ser Gly Gly Thr Thr Thr Tyr Ala Asp Ser Val Lys
1               5                   10                  15

Gly


<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ser Ala Ala Ser Ser Tyr
1               5


<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ala Ser Gln Gly Ile Ser Asn Tyr Leu Ala
1               5                   10


<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ala Ser Thr Leu Gln Ser
1               5


<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Gln Leu Ile Ser Tyr Pro Phe Thr
1               5
```

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Gln Tyr Asn Met Thr
1 5

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Ser Ile Tyr Ser Ser Gly Gly Val Thr Pro Tyr Ala Asp Ser Val Lys
1 5 10 15

Gly

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Gly Arg Leu Leu Phe Asp Tyr
1 5

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Arg Ala Ser Gln Ser Ile Ser Asn Tyr Leu Asn
1 5 10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

Ala Ala Ser Ser Leu Gln Ser
1 5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Gln Gln Gly Tyr Thr Ala Pro Arg Ser
1 5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Asn Tyr Gln Met Asp
1 5

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Tyr Ile Gly Pro Ser Gly Gly Arg Thr Lys Tyr Ala Asp Ser Val Lys
1 5 10 15

Gly

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Gly Leu Tyr Ser Phe Asp Tyr
1 5

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Arg Ala Gly Gln Ser Ile Ser Asn Phe Leu Asn
1 5 10

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Ala Ala Ser Ser Leu Gln Ser
1 5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 36

Gln Gln Ser Tyr Ser Thr Pro Phe Thr
1 5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 37

Asn Tyr Trp Met Gly
1 5

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 38

Tyr Ile Arg Ser Ser Gly Gly Leu Thr His Tyr Ala Asp Ser Val Lys
1 5 10 15

Gly

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 39

Gly Leu Tyr Ser Phe Asp Tyr
1 5

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 40

Arg Ala Ser Gln Gly Val Asn Asn Phe Leu Ala
1 5 10

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic

```
      peptide

<400> SEQUENCE: 41

Ala Ala Ser Thr Leu Gln Ser
1               5


<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Gln Ser Tyr Ser Thr Pro Arg Gly
1               5


<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Val Gln Leu Leu Glu Ser Gly Gly Gly
1               5                   10
```